United States Patent
Angenent et al.

(10) Patent No.: US 9,650,652 B2
(45) Date of Patent: May 16, 2017

(54) PRODUCTION OF CARBOXYLATES AND METHANE FROM BIOMASS WASTE

(75) Inventors: Largus T. Angenent, Ithaca, NY (US); Matthew T. Agler, Aachen (DE)

(73) Assignee: Cornell University, Ithaca, NY (US)

( * ) Notice: Subject to any disclaimer, the term of this patent is extended or adjusted under 35 U.S.C. 154(b) by 257 days.

(21) Appl. No.: 14/237,611

(22) PCT Filed: Aug. 8, 2012

(86) PCT No.: PCT/US2012/050034
§ 371 (c)(1),
(2), (4) Date: May 13, 2014

(87) PCT Pub. No.: WO2013/022998
PCT Pub. Date: Feb. 14, 2013

(65) Prior Publication Data
US 2014/0322772 A1    Oct. 30, 2014

Related U.S. Application Data

(60) Provisional application No. 61/521,603, filed on Aug. 9, 2011.

(51) Int. Cl.
| | | |
|---|---|---|
| C12P 7/40 | (2006.01) | |
| C12M 1/107 | (2006.01) | |
| C12N 1/32 | (2006.01) | |
| C07C 51/48 | (2006.01) | |
| C12M 1/34 | (2006.01) | |
| C12M 1/00 | (2006.01) | |
| C12P 5/02 | (2006.01) | |

(52) U.S. Cl.
CPC ............... *C12P 7/40* (2013.01); *C07C 51/48* (2013.01); *C12M 21/04* (2013.01); *C12M 41/12* (2013.01); *C12M 41/26* (2013.01); *C12M 41/40* (2013.01); *C12M 47/10* (2013.01); *C12N 1/32* (2013.01); *C12P 5/023* (2013.01); *Y02E 50/343* (2013.01)

(58) Field of Classification Search
CPC   C12P 5/023; C12P 7/40; C07C 51/48; C12M 21/04; C12M 41/12; C12M 41/26; C12M 41/40; C12M 47/10; C12N 1/32; Y02E 50/343
USPC ......................................................... 435/136
See application file for complete search history.

(56) References Cited

U.S. PATENT DOCUMENTS

| | | | | |
|---|---|---|---|---|
| 4,398,039 | A * | 8/1983 | Pesa ...................... | C07C 29/149 502/328 |
| 2008/0176301 | A1* | 7/2008 | Granda ................. | C12M 21/04 435/157 |
| 2008/0280338 | A1 | 11/2008 | Hall et al. | |
| 2008/0311640 | A1* | 12/2008 | Cox ......................... | C12P 3/00 435/168 |
| 2009/0239279 | A1 | 9/2009 | Hall et al. | |
| 2010/0317071 | A1 | 12/2010 | Hamelers et al. | |

FOREIGN PATENT DOCUMENTS

WO         2007136762 A2     11/2007

OTHER PUBLICATIONS

Domke et al. Mixed acid fermentation of paper fines and industrial biosludge. Bioresource Technology (2004), v91, p. 41-51.*
Wang et al. Extraction Equilibria of Monocarboxylic Acids with Trialkylphosphine Oxide. J. CHem. Eng. Data (2001), v46, p. 831-837.*
Schlosser et al. Recovery and separation of organic acids by membrane-based solvent extraction and pertraction: An overview with a case study on recovery of MPCA. Separation and Purification Technology ()2005), v41, p. 237-266.*
Kenealy et al. Production of caproic acid by cocultures of ruminal cellulolytic bacteria and Clostridium kluyveri grown on cellulose and ethanol. Appl Microbiol Biotechnol (1995), v44, p. 507-513.*
Agler, Matthew, et al., Waste to bioproduct conversion with undefined mixed cultures: the carboxylate platform, Trends in Biotechnology, Feb. 2011, vol. 29, No. 2, pp. 70-78.
Hollister, Emily B., et al., Structure and dynamics of the microbial communities underlying the carboxylate platform for biofuel production, Appl. Microbiol. Biotechnol., Jul. 31, 2010, vol. 88, pp. 389-399.
Levy, P.F., et al., Biorefining of biomass to liquid fuels and organic chemicals, Enzyme and Microbial Technology, Jul. 1981, vol. 3, pp. 207-215.
Steinbusch, Kirsten, et al., Biological formation of caproate and caprylate from acetate: fuel and chemical production from low grade biomass, Energy & Environmental Science, Nov. 11, 2010, vol. 4, pp. 216-224.

* cited by examiner

*Primary Examiner* — Scott Long
*Assistant Examiner* — Sean C Barron
(74) *Attorney, Agent, or Firm* — Hodgson Russ LLP

(57) ABSTRACT

Methods and systems for producing and removing $C_6$ and/or $C_8$ carboxylates and/or methane from carbohydrate containing biomass, an alcohol, and mixtures of microorganisms under an anaerobic environment. The $C_6$ and/or $C_8$ carboxylates are removed continuously or in-line. Methanogenesis is not inhibited and very little input carbon is lost as carbon dioxide.

15 Claims, 12 Drawing Sheets

PRODUCTION OF CARBOXYLATES AND METHANE FROM BIOMASS WASTE

CROSS-REFERENCE TO RELATED APPLICATIONS

This application claims priority to U.S. provisional patent application No. 61/521,603, filed Aug. 9, 2011, the disclosure of which is incorporated herein by reference.

STATEMENT REGARDING FEDERALLY SPONSORED RESEARCH

This invention was made with government support under contract no. 2007-35504-05381 awarded by the United States Department of Agriculture (USDA). The government has certain rights in the invention.

FIELD OF THE INVENTION

The present invention generally relates to the field of obtaining selected carboxylates from biomass. More particularly, the present invention relates to methods for obtaining medium chain carboxylates from carbohydrate containing biomass.

BACKGROUND OF THE INVENTION

Current anaerobic digester technology can convert organic waste into the energy carrier methane. However, methane is not an ideal transportation fuel and the economic value of methane is too low to support widespread adaptation. In the last decade, especially in dry-mill technology (i.e., grinding kernel and subsequent yeast fermentation), funds for liquid biofuel production have been mostly invested in the corn kernel-to-ethanol industry. However, the net energy balance ratio (i.e., renewable energy out over nonrenewable energy in) has been low; in large part, because of the vast energetic costs to separate (i.e., distill) miscible ethanol.

Current practice and belief is that methanogenesis should be completely inhibited during production of medium chain carboxylates. Medium-chain carboxylic acids, such as n-caproic acid, are commodity chemicals that are already used in lubricants, personal care products, animal feed additives, and antimicrobials. The $C_6$ carboxylate, n-caproic acid, can be converted to a fuel by, for example, a series of ketonization and dehydrogenation processes to generate alkanes ($C_{11}$ alkane is a drop in fuel). These alkanes can be blended with other chemicals to produce a transportation fuel, such as biodiesel. The value of n-caproic acid is already 20 times higher than methane. The relatively low maximum solubility of n-caproic acid makes extraction easier and with a much lower energy footprint compared to distillation of miscible ethanol.

Although the value of medium chain carboxylates as energy chemicals is recognized, efficient and economically feasible methods for producing these are not available. Fermentation of lignocellulosic substrates to carboxylic acid acids (e.g., acetate, butyrate) has not been very efficient. Additionally, carbon is lost as $CO_2$. The same is true for anaerobic digestion: digestion of carbohydrates results in methane while half of the input carbon is lost as $CO_2$.

BRIEF SUMMARY OF THE INVENTION

The present invention provides methods and systems for producing and sequestering liquid biochemicals from biomass using microbial mixtures under a controlled environment. The method comprises contacting microorganisms with biomass in the presence of one or more electron donors under conditions such that medium chain carboxylates (e.g., $C_4$ to $C_8$) are produced and can be isolated.

In one embodiment, the method for obtaining a product comprising $C_6$ and/or $C_8$ carboxylates and/or methane from a carbohydrate containing biomass comprises the steps of: a) contacting the carbohydrate containing biomass, an alcohol, and a mixture of microorganisms in a vessel to form a reaction mixture; b) maintaining the reaction mixture under anaerobic conditions at a temperature of from 15° C. to 40° C., a pH of from 4 to 6, and a hydrogen partial pressure of from 0.2 atm to 5 atm for a period of time such that $C_6$ and/or $C_8$ carboxylates and/or methane are formed in the reaction mixture, and; c) removing at least a portion of the $C_6$ and/or $C_8$ carboxylates and/or methane.

In one embodiment, the invention provides a system for producing $C_6$ and/or $C_8$ carboxylates from a reaction mixture. In another embodiment, the invention provides a system for producing $C_4$ to $C_8$ carboxylates, methane, or a combination thereof from a reaction mixture.

DETAILED DESCRIPTION OF THE INVENTION

Figure 1:
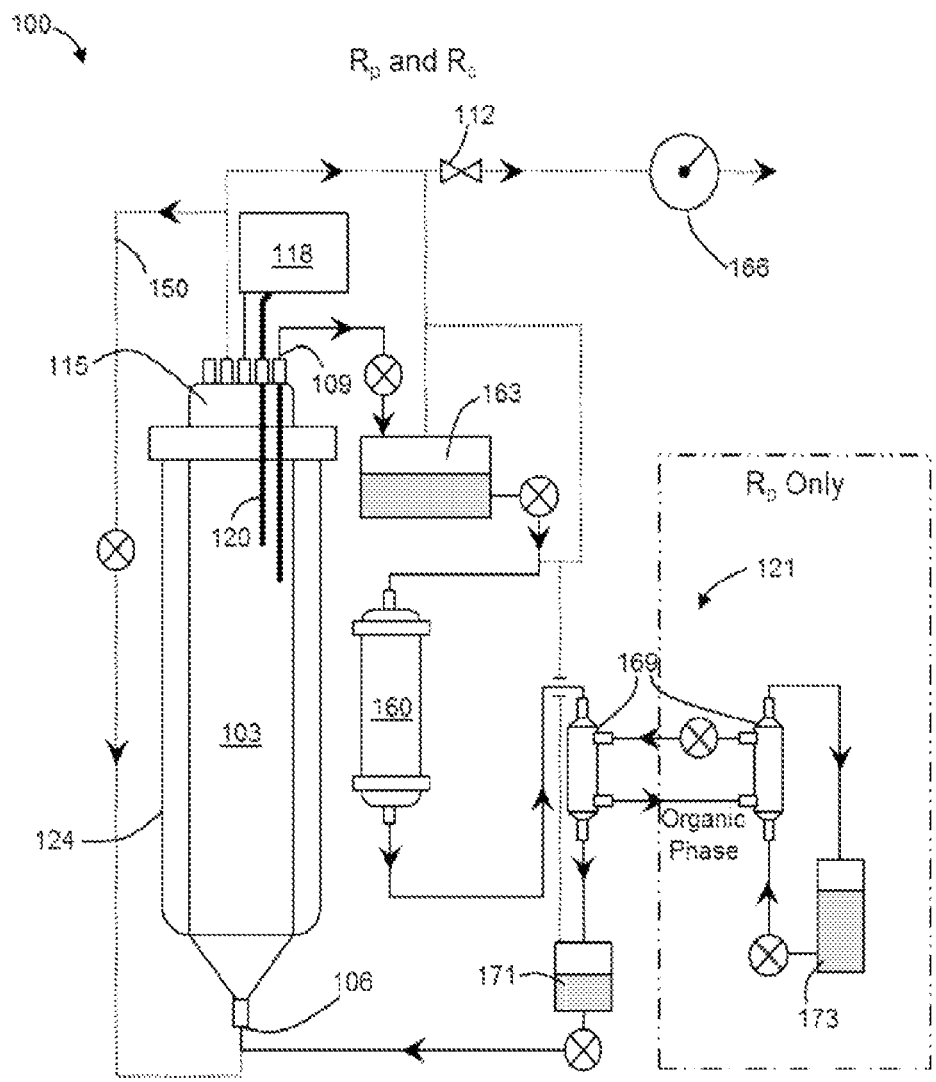
FIG. 1. Representative diagram of a system according to an embodiment of the present invention, wherein dotted lines depict gas conduits and solid lines depict liquid conduits.

The present invention provides methods and systems for producing and sequestering liquid biochemicals from biomass using microbial mixtures under a controlled environment. In one embodiment, the method involves producing short-chain carboxylic acids from biomass, and elongating the short chain carboxylic acids to more hydrophobic, extractable medium-chain carboxylic acids. The method comprises contacting microorganisms with biomass in the presence of an electron donor under conditions such that medium chain carboxylates are produced and can be extracted.

In the present invention we observed that there was no need for inhibition of methanogenesis for the continuous production of $C_4$ to $C_8$ carboxylates. Further, it was observed that if methanogenesis is allowed to occur, there was essentially no loss of input carbon as waste $CO_2$ Hydrogenotrophic methanogenesis, or ethanol to methane conversion, is not stopped and methane is generated, thereby forming two valuable fuels, carboxylates and methane. By "essentially no loss", it is meant that less than 5% of input carbon is lost as waste $CO_2$.

The term "carboxylate" as used herein, unless otherwise stated, is meant to refer to linear carboxylic acids or carboxylic acid salts.

It may seem counter intuitive to produce medium-chain organic acids rather than to produce ethanol. However, producing these acids using ethanol will not only result in a more broadly used product but also has potential cost and energy savings because the former is less costly to recover than ethanol. In addition, more carbon in the product will be generated than available in the added ethanol.

Without intending to be bound by any particular theory it is considered that the reactions involved in the present method are as follows:

Lignocellulose→(hydrolysed via chemical and microbial pretreatment) monomers (sugars and other monomers). Glucose conversion is shown below but the scheme applies to others sugars also.

$$C_6H_{12}O_6 \rightarrow 3CH_4 + 3CO_2 \quad \text{(Eqn 1)}$$

$$C_6H_{12}O_6 \rightarrow C_4H_8O_2 + 2CO_2 + 2H_2 \quad \text{(Eqn 2)}$$

A process that allows hydrogenotrophic methanogens to reduce $CO_2$ to $CH_4$ and that derives the extra needed reducing equivalents from ethanol is described below:

$$\begin{aligned}
C_6H_{12}O_6 &\rightarrow C_4H_8O_2 + 2\,CO_2 + 2\,H_2 & \text{(Eqn 2)} \\
8H_2 + 2CO_2 &\rightarrow 2CH_4 + 4H_2O \\
\underline{3C_2H_6O + 3H_2O} &\underline{\rightarrow 3C_2H_4O_2 + 6H_2} & \text{(Eqn 3)} \\
C_6H_{12}O_6 + 3C_2H_6O &\rightarrow C_4H_8O_2 + \\
& 3C_2H_4O_2 + 2CH_4 + H_2O
\end{aligned}$$

Further, excess ethanol drives chain-elongation reactions, which can elongate product molecules, such as acetate (Eqn 3), to the desired product (e.g., n-butyrate, n-caproate ($C_6$) or n-caprylate($C_8$)) by adding two carbon atoms to the chain, which via product-specific extraction can be stopped at the desired step:

$$\begin{aligned}
C_6H_{12}O_6 + 3C_2H_6O &\rightarrow C_4H_8O_2 + 3C_2H_4O_2 + 2CH_4 + H_2O & \text{(Eqn 3)}\\
3C_2H_4O_2 + 3C_2H_6O &\rightarrow 3C_4H_8O_2 + 3H_2O \\
3C_4H_8O_2 + 3C_2H_6O &\rightarrow 3C_6H_{12}O_2 + 3H_2O \\
\underline{3C_6H_{12}O_2 + 3C_2H_6O} &\underline{\rightarrow 3C_8H_{16}O_2 + 3H_2O} & \text{(Eqn 4)}\\
C_6H_{12}O_6 + 12C_2H_6O &\rightarrow C_4H_8O_2 + \\
& 3C_8H_{16}O_2 + 2CH_4 + 10H_2O
\end{aligned}$$

In an aspect, the present invention provides methods for producing and sequestering carboxylates (e.g., C3 to C8 carboxylates) from biomass using microorganisms. In one embodiment, the method for obtaining a product comprising $C_6$ and/or $C_8$ carboxylates and methane from a carbohydrate containing biomass comprises the steps of: a) contacting the carbohydrate containing biomass, an alcohol, and a mixture of microorganisms in a vessel to form a reaction mixture under anaerobic conditions; b) maintaining the reaction mixture from 15° C. to 40° C., a pH of from 4 to 6, and a hydrogen partial pressure of from 0.2 atm to 5 atm for a period of time such that products comprising $C_6$ and/or $C_8$ carboxylates and methane are formed in the reaction mixture, and; c) separating the $C_6$ and/or $C_8$ carboxylates and/or methane. In various embodiments, the invention provides a method for forming $C_6$ and/or $C_8$ carboxylates and/or methane from a carbohydrate containing biomass where less than 5.0%, 4.5%, 4.0%, 3.5%, 3.0%, 2.5%, 2.0%, 1.5%, 1.0%, 0.5% of input carbon is lost as carbon dioxide. In various other embodiments, the invention provides a method for forming $C_6$ and/or $C_8$ carboxylates and/or methane from a carbohydrate containing biomass where less than 0.5%, 0.4%, 0.3%, 0.2%, 0.1% of input carbon is lost as carbon dioxide. In yet another embodiment, none of the carbon is lost as carbon dioxide. In one embodiment, the method can be conducted to obtain and remove $C_4$ carboxylates.

The method of the present invention is conducted in a vessel under anaerobic conditions. For example, anaerobic conditions can be achieved by sealing the vessel and the system except to allow products (both liquid products and gas products) to be separated or escape. As used herein "vessel" refers to a reaction flask, reactor, or any other container and is meant to refer to a single vessel or more than one vessel (e.g., reactor network) for carrying out different stages of the reaction or all stages of the reaction. The reactants or contents of the vessel can be made of a number of different materials. For example, the vessel can be glass or stainless steel and constructed as to prevent diffusion through fittings and withstand pressurization. The vessel can be mixed periodically to promote substrate-microorganism contact.

Various sources of carbohydrate containing biomass can be used. For example, carbohydrate containing biomass can be municipal waste (food, yard, paper, organic fraction of source-sorted garbage, wood or biomass-based building materials, compost feedstocks), animal waste, agricultural residues (e.g., corn stover, corn fiber, wheat, barley, or rye straw, hay, silage, fruit or vegetable processing wastes), by-products of alternative energy processes (corn beer, sugar cane bagasse, butanol beer), wood wastes (e.g., saw mill, paper wastes, wooden pallets, building materials), biosolids wastes (waste activated sludge), animal hydrolysates (dead animals made soluble), waste from food production, such as cheese whey, yogurt production waste, beer production waste (including spent grain), or animal rendering waste. The carbohydrate containing biomass may contain lignocellulose.

The carbohydrate containing biomass (i.e., substrate) loading rate of the method can vary depending on the size of the reactor. Generally, lower loading rates usually correspond to higher efficiencies. The loading rate can also influence the microbial community makeup. In one embodiment, the loading can be from 10 g/L/d to 50 g/L/d and all values to the 0.1 g/L/d and ranges therebetween. In one embodiment, the loading rate can be varied from 1 to 10 g total chemical oxygen demand (TCOD) $L^{-1}\,d^{-1}$ in 4 steps. Some amount of settling time may be required for the biomass within the vessel after it is added. In one embodiment, the settling time is between 0.1 and 2 hours, including all values to 0.1 hour and ranges therebetween. In another embodiment, the settling time is 1 hour. In yet another embodiment, the settling time is less than 1 hour. Settling time can be dependent on, for example, the size of the vessel and the amount of biomass used.

Various electron donors can be used. The term "electron donor" is meant to include compounds that when oxidized can donate hydrogen or electrons to the carboxylate elongation process. In one embodiment, the electron donor is an alcohol. In another embodiment, the alcohol can be a $C_2$ to $C_4$ alcohol. Suitable electron donors include ethanol, lactate, butanol, glycerol, and other alcohols. In one embodiment, ethanol is the electron donor.

The ethanol (i.e., electron donor) can come from a feedstock. For example, the ethanol feedstock can be added to the vessel or be produced in-situ (e.g., fermentation). For example, the ethanol feedstock can be corn-to-ethanol beer, whiskey or other grain-based alcohol mash, grain-based beer used for making beer, or fermentation broth from microbes that can synthesize ethanol and other alcohols. In one embodiment, the method to form $C_6$ and/or $C_8$ carboxylates can further comprise incorporation of a dry mill plant, to upgrade beer (ethanol, organic material, and solids) to a higher value liquid biofuel product. In one embodiment, ethanol is provided such that all ethanol is consumed and all formed organic acids during conversion of carbohydrate containing biomass to intermediates are elongated completely to $C_6$ and/or $C_8$ carboxylates.

The microorganisms of the invention are those that effect chain elongation by oxidizing ethanol (or other electron donor) and transferring reducing equivalents (e.g., electrons, hydrogen, organic intermediates) to the carboxylate elongation (i.e., converting shorter carboxylates to longer chain carboxylates) process, which may be either in the microorganism that does ethanol oxidation or in a different microorganism. In one embodiment, the mixture of microorganisms comprises microorganisms capable of effecting $C_6$ and/or $C_8$ carboxylate formation, and/or fermentation of biomass, and/or converting carbon dioxide to methane. The reaction can be carried out by the same microorganisms or different microorganisms. It is important to note that pure cultures of microorganisms are not needed to carry out the method and thus the inoculum source need not be sterile. As used herein "inoculum source" means an original source of a complex microbial community, which does not limit the final composition of the microbial community. The final composition is determined by reactor operating conditions and productivity. Without intending to be bound by any particular theory it is considered that the advantages of using open cultures of microbial consortia (also referred to as open reactor microbiomes or microbial microbioto) compared to pure cultures lies in their ability to: i. incorporate carbon from complex streams due to a broad-substrate spectrum; ii. maintain functionality even with nonsterile input; and iii. be resilient in response to disturbances.

Various microorganisms and mixtures of microorganisms can be used. For example, the microorganisms can be bacteria, methanogens, archaea, eukaryotic, or combinations thereof. The mixture of microorganisms can comprise one or more of bacteria, methanogens, archaea, or eukaryotic organisms. In various embodiments, the microorganisms are be open cultures of microbial consortia. The microorganism can be selected from the phyla Acidobacteria, Actinobacteria, Bacteroidetes, Caldiserica, Chloroflexi, Cyanobacteria, Deferribacteres, EM3, Fibrobacteres, Firmicutes, Nitrospirae, OP10, OP8, OP9, Proteobacteria, Spirochaetes, Synergistetes, TG3, TM7, Tenericutes, Thermi, Thermotogae, Verrucomicrobia, WPS-2, or a combination thereof. In one embodiment, the microorganism can be selected from the family Acetobacteraceae, Actinomycetaceae, Aerococcaceae, Aeromonadaceae, Alcaligenaceae, Alicyclobacillaceae, Anaerobaculaceae, Anaerobrancaceae, Anaerolinaceae, Anaeroplasmataceae, Aurantimonadaceae, Bacillaceae, Bacteroidaceae, Bdellovibrionaceae, Beijerinckiaceae, Bifidobacteriaceae, Bradyrhizobiaceae, Brevibacteriaceae, Brucellaceae, Burkholderiaceae, Caldicellulosiruptoraceae, Caldilineaceae, Campylobacteraceae, Carnobacteriaceae, Catabacteriaceae, Caulobacteraceae, Cellulomonadaceae, Clostridiaceae, Clostridiales_Family_XI_Incertae_Sedis, Clostridiales_Family_XIII_Incertae_Sedis, Comamonadaceae, Coriobacteriaceae, Corynebacteriaceae, D2, Deferribacteraceae, Deinococcaceae, Desulfomicrobiaceae, Desulfurellaceae, Dethiosulfovibrionaceae, Dietziaceae, Enterobacteriaceae, Enterococcaceae, Erysipelotrichaceae, Eubacteriaceae, Fibrobacteraceae, Flammeovirgaceae, Flavobacteriaceae, Flexibacteraceae, Halanaerobiaceae, Helicobacteraceae, Hydrogenophilaceae, Hyphomicrobiaceae, Hyphomonadaceae, Intrasporangiaceae, Lachnospiraceae, Lactobacillaceae, Leptospiraceae, Leuconostocaceae, Listeriaceae, Marinilabiaceae, Methylobacteriaceae, Methylocystaceae, Methylophilaceae, Microbacteriaceae, Micrococcaceae, ML1228J-1, Moraxellaceae, Mycoplasmataceae, Nitrosomonadaceae, Nocardiaceae, Nocardioidaceae, otu_1038, otu_1286, otu_1301, otu_1313, otu_1352, otu_1368, otu_1942, otu_1943, otu_1944, otu_2199, otu_2210, otu_2211, otu_2234, otu_2328, otu_2331, otu_2332, otu_2379, otu_4175, otu_4231, otu_4232, otu_4233, otu_4234, Oxalobacteraceae, Paenibacillaceae, Patulibacteraceae, Peptococcaceae, Phormidiaceae, Phyllobacteriaceae, Planococcaceae, Porphyromonadaceae, Prevotellaceae, Promicromonosporaceae, Propionibacteriaceae, Pseudomonadaceae, Rhizobiaceae, Rhodobacteraceae, Rhodocyclaceae, Rhodospirillaceae, Rikenellaceae, Ruminococcaceae, Sanguibacteraceae, Saprospiraceae, SHA-31, Sinobacteraceae, Solibacteraceae, Sphaerochaetaceae, Sphingobacteriaceae, Sphingomonadaceae, Spirochaetaceae, Streptococcaceae, Succinivibrionaceae, Symbiobacteriaceae, Synergistaceae, *Syntrophomonadaceae,* Thermoanaerobacteraceae, Thermoanaerobacterales_Family_III_Incertae_Sedis, Thermodesulfobiaceae, Thermodesulfovibrionaceae, Thermotogaceae, Thermovirgaceae, Thiotrichaceae, TTA_B6, vadinHA31, Veillonellaceae, Verrucomicrobiaceae, Xanthobacteraceae, Xanthomonadaceae, YAB3B13, or combinations thereof. In one embodiment, the mixture of microorganisms comprises Clostridiaceae, Peptococcaceae, Ruminococcaceae, *Syntrophomonadaceae,* Thermoanaerobacteraceae, other Clostridiales, other Clostridia, other Phyla, or combinations thereof. In another embodiment, the mixture of microorganisms can be Clostridiaceae, Peptococcaceae, Thermoanaerobacteraceae, Actinobacteridae, Lactobacillaceae, other Actinobacteria, other Bacilli, other Clostridiales, other Clostridia, other Phyla, or combinations thereof. In another embodiment, the mixture of microorganisms can comprise Ruminococcaceae and *Clostridium kluyveri.* In another embodiment, the mixture of microorganisms can comprise *Clostridium kluyveri.* In yet another embodiment, the mixture of microorganisms can comprise *Escherichia coli.* Without intending to be bound by any particular theory it is considered that a mixture of microorganisms are used to provide a more stable process during extraction with an organic phase that is toxic to pure cultures.

The microorganisms of the invention can be obtained from a number of inoculum sources such as activated sludge, anaerobic digesters, acidogenic processes, rumen microbes, soil microorganisms, marine microorganisms, intestinal microorganisms (from animals or insects), and feces. In the method of the present invention, the relative population of the microorganisms can be manipulated by controlling the pH, temperature, $H_2$ partial pressure, and mixture of microorganisms in an anaerobic environment. Without intending to be bound by any particular theory, it is considered that by adjusting the reactor environment the composition of the final microorganism community is controlled. The inoculum source does not limit the composition of the final community. Adjustment of these parameters causes certain parts of the microbial community to shift their metabolism in order to maintain optimum growth and productivity. This shift cascades through the community and causes changes in the other parts of the community that are metabolically connected to one another. Changes in the environment within the vessel cause the community to "automatically" optimize to produce the product that is selected for by operators.

To carry out the method of the present invention, in one embodiment, the temperature within the vessel is maintained at mesophilic conditions. The reaction is conducted at from 15° C. to 40° C., including all values to the 0.1° C. and ranges therebetween. In another embodiment, the reaction can be conducted at from 18° C. to 37° C. including all values to the 0.1° C. and ranges therebetween. Optionally, the reaction mixture can be held at thermophilic temperatures prior to being maintained at from 15° C. to 40° C., including all values to the 0.1° C. and ranges therebetween, to promote microorganism population growth during primary fermentation. In one embodiment, the thermophilic temperature can be from 40° C. to 55° C., including all values to the 0.1° C. and ranges therebetween.

The pH of the reaction should be maintained from 4 to 6, including all values to the tenth decimal place and ranges therebetween. In one embodiment, the pH is controlled to prevent growth of acetoclastic methanogens and other competing pathways by adding concentrated acid or base as needed. In another embodiment, the pH is from 4 to 5.5, including all values to the tenth decimal place and ranges therebetween.

The hydrogen partial pressure can be varied by, for example, pressurizing the headspace via a pressure relief valve and recycling the gas product through a scrubbing solution of KOH to remove $CO_2$. In one embodiment, the $H_2$ partial pressure can be from 0.2 atm to 5 atm including all values to the 0.1 atm and ranges therebetween. In another embodiment, the $H_2$ partial pressure can be from 0.2 atm to 2 atm including all values to the 0.1 atm and ranges therebetween. It is considered the $H_2$ partial pressure leads to: (1.) thermodynamic selection for n-butyrate over acetate in primary fermentation; (2.) drive acetate chain elongation (to n-butyrate); and (3.) drive chain elongation of n-butyrate to form n-caproate ($C_6$).

The method of the invention can be carried out continuously or semi-continuously. Semi-continuously includes all batch-wise processes. In one embodiment, the vessel is fed semi-continuously or continuously with organic waste as the primary substrate and ethanol to supply reducing equivalents for methane generation and chain elongation. The vessel may be fed every 1 to 5 days. In various embodiments, the vessel is fed every day, every two days, or every three days. The mixtures of microorganisms are added at the beginning of the reaction and get replenished by their own reproduction.

The method can be carried out indefinitely (e.g., years) with hydraulic retention times of from 4 to 24 hours or up to 40 days. The hydraulic retention time is the residence time of the biomass required to effect a desired production of the products. In one embodiment, the hydraulic retention time can be from 8 days to 15 days. The hydraulic retention times used in the method can be varied. For example, hydraulic retention times can vary due to the size of the vessel or composition of the biomass.

The products formed from the present method comprise a liquid component and a gaseous component. The liquid component can contain, for example, $C_4$, $C_5$, $C_6$, $C_7$, $C_8$ carboxylates, methane, and a combination thereof. It was surprisingly observed that $C_6$ and/or $C_8$ carboxylate production can be increased by maximizing the rate of extraction of carboxylates. Without intending to be bound by any particular theory it is considered that extraction of carboxylates may reduce the toxic effects of the carboxylates to microorganisms in the reactor. As a result, rates of chain elongation and $CO_2$ reduction to methane are maintained or increased. In various embodiments, particulate matter is present in the liquid component and can range from mainly substrate, leftover substrate, or biomass. The particulate matter can be used as compost.

The gaseous component of the product can comprise methane and carbon dioxide. The methane can be present in greater than 99% of the total gaseous component. It is preferred that the carbon dioxide produced be present in less than 5% of the total gaseous component.

The gaseous component can, optionally, be captured and collected. For example, the methane produced during the production of $C_6$ and/or $C_8$ carboxylates can be collected. Alternatively, the methane from the production of $C_6$ and/or $C_8$ carboxylates can be recycled back into the vessel. The carbon dioxide can be removed from the gaseous component via a basic scrubbing solution. For example, the scrubbing solution can be a potassium hydroxide (KOH) solution.

Therefore, in an aspect, the invention provides product made by the process disclosed herein. In one embodiment, the invention provides a liquid component comprising $C_6$ and $C_8$ carboxylates. In one embodiment, the method provides a liquid component comprising $C_6$ carboxylates. In another embodiment, the invention provides a liquid component comprising $C_8$ carboxylates. In yet another embodiment, the invention provides a liquid component comprising $C_4$ to $C_8$ carboxylates.

In one embodiment, the invention provides a product comprising from 50% to 99% $C_6$ carboxylates, including all values to the 0.1% and ranges therebetween. In one embodiment, the invention provides a product comprising from 50% to 99% $C_8$ carboxylates, including all values to the 0.1% and ranges therebetween. In one embodiment, the invention provides a product comprising greater than 99% $C_6$ carboxylates. In one embodiment, the invention provides a product comprising greater than 99% $C_8$ carboxylates. In one embodiment, the invention provides a product comprising from 50% to 99% $C_6$ and $C_8$ carboxylates, including all values to the 0.1% and ranges therebetween. In one embodiment, the invention provides a product comprising greater than 99% $C_6$ and $C_8$ carboxylates.

The products (e.g., $C_6$ carboxylates and/or $C_8$ carboxylates) can be removed in-line in a continuous manner from the system. In one embodiment, at least a portion of the $C_6$ carboxylates and/or $C_8$ carboxylates is removed from the reaction mixture. In various other embodiments, at least 80%, 85%, 90%, 91%, 92%, 93%, 94%, 95%, 96%, 97%, 98%, 99% of the $C_6$ carboxylates and/or $C_8$ carboxylates are removed from the reaction mixture. In yet another embodiment, all of the $C_6$ carboxylates and/or $C_8$ carboxylates are removed from the reaction mixture.

Carboxylate removal (e.g., pertraction) while maintaining anaerobic conditions in the vessel simultaneously promotes parallel $CO_2$ reduction to ethanol and chain elongation. In one embodiment, the $C_6$ and $C_8$ carboxylates are removed by a membrane-based liquid-liquid extraction using a mineral oil stripping solution comprising a phosphine oxide. For example, the phosphine oxide is trioctylphosphine oxide (TOPO). In various other embodiments, the stripping solution can comprise, for example, tributylphosphine, alamine, aliquat solvents (e.g., tertiary and quaternary amines), methyl t-butyl ether (MTBE), hexane, other organic solvents, and ionic liquids. The extraction system operates on a pH gradient, where undissociated acids in the reactor pass into the organic solvent. All acids in the stripping solution are dissociated due to the alkaline pH, so a concentration gradient drives them back into aqueous solution. The pH in the reactor must be low enough (e.g., less than pH 6) that a fraction of carboxylates are undissociated. The stripping solution is preferentially maintained at pH greater of 8.0 or above for removal of the carboxylates.

In one embodiment, continuous carboxylate removal can be performed using hollow-fiber membrane sizes and pumping rates using mineral oil/TOPO pertraction system. Ionic liquid candidates as an organic phase can be used instead of mineral oil/TOPO. For example, CYPHOS IL 104 (CAS 46552759-7; Strem Chemicals, Newburyport, Mass.) immobilized on XAD4 resin can be used. Other suitable ionic liquids include CYPHOS IL 102 (with a chloride anion instead of the organic anion in 104) and imidazolium-based ionic liquids.

$CO_2$ scrubbing with KOH solution can provide a potential advantage of increasing $H_2$ headspace partial pressure, and can reduce the rates of autotrophic acetogenesis and methanogenesis (which also consumes $H_2$). If the hydrogen balance is sufficient, such that excess $H_2$ is available, the KOH stripping step may not be needed. However, if $H_2$ levels are insufficient, scrubbing $CO_2$ is useful for controlling $H_2$ levels and driving chain elongation with ethanol.

The carboxylates can be removed by methods other than membrane-based liquid pertraction methods, for example, using ionic liquids immobilized onto a stationary phase in an in-line column. For example, the carboxylates of the invention can be removed by other solvent extraction methods with or without membranes (i.e., direct liquid/liquid solvent extraction or supported liquid membranes), electrochemical methods, extraction through prevaporation, and adsorption on an ion exchange media (e.g., ionic liquid).

The system of the present invention can involve a single or multiple reactor. For example, the carboxylic acids (e.g., acetate, butyrate) can be pre-made in a separate reactor and a secondary reactor can carry out the chain elongation process.

The carboxylates produced by the present method can be used for various applications. Additionally, the carboxylates can be converted into alkanes for biofuel. For example, the carboxylates can be converted to alkanes by a subsequent abiotic process (e.g., ketonization). In one embodiment, other valuable carboxylates can be produced instead by altering the organic loading rate or pH of the system.

In one embodiment, the present invention provides a method for indirect recovery of cellulosic ethanol without the need for distillation and incorporates production of cellulosic ethanol as an intermediate product in the process.

In an aspect, the invention provides a system for producing $C_4$, $C_5$, $C_6$, $C_7$, $C_8$ carboxylates, methane, or a combination thereof. The system is useful for producing such products from a reaction mixture.

The steps of the method described in the various embodiments and examples disclosed herein are sufficient to produce the products of the present invention. Thus, in one embodiment, the method consists essentially of a combination of the steps of the method disclosed herein. In another embodiment, the method consists of such steps.

In one embodiment (depicted in FIG. 1), the invention provides a system 100 for producing $C_6$ and/or $C_8$ carboxylates from a reaction mixture, the system 100 comprising: a vessel 103 for containing the reaction mixture under anaerobic conditions, the vessel 103 having: an entrance orifice 106 for receiving components of the reaction mixture; and an exit orifice 109 for removing fluid from the vessel; a control valve 112 in pneumatic communication with a headspace 115 of the vessel 103 and configured to maintain a $H_2$ partial pressure within the headspace of from 0.2 to 5 atm; a pH controller 118 configured to maintain a pH of the reaction mixture from 4 to 6; and a separation device (shown generally as 121) configured to receive a carboxylate-containing fluid from the vessel 103 by way of the exit orifice 109, separate at least a portion of the $C_6$ and/or $C_8$ carboxylates from the received fluid, and return the remainder fluid to the vessel 103 by way of the entrance orifice 106. The system 100 may have a gas flow meter 166 for measuring the flow of gas released (i.e., not recycled) from the system 100. The system 100 may have an inlet 104 for adding fresh material(s) (e.g., biomass) to the vessel and an outlet 105 for removing spent material(s) from the vessel.

In an example, the reaction mixture of the system 100 comprises carbohydrate containing biomass, an alcohol, and a mixture of microorganisms. The carbohydrate containing biomass, an alcohol, and a mixture of microorganisms are as defined above.

The system 100 can further include a temperature element 124 configured to maintain a temperature of from 15° C. to 40° C. within the vessel 103. The temperature element 124 can be a heating/cooling jacket covering at least a portion of the vessel 103, a heating/cooling element within the vessel 103, or heating/cooling element underneath the vessel 103.

Figure 2:
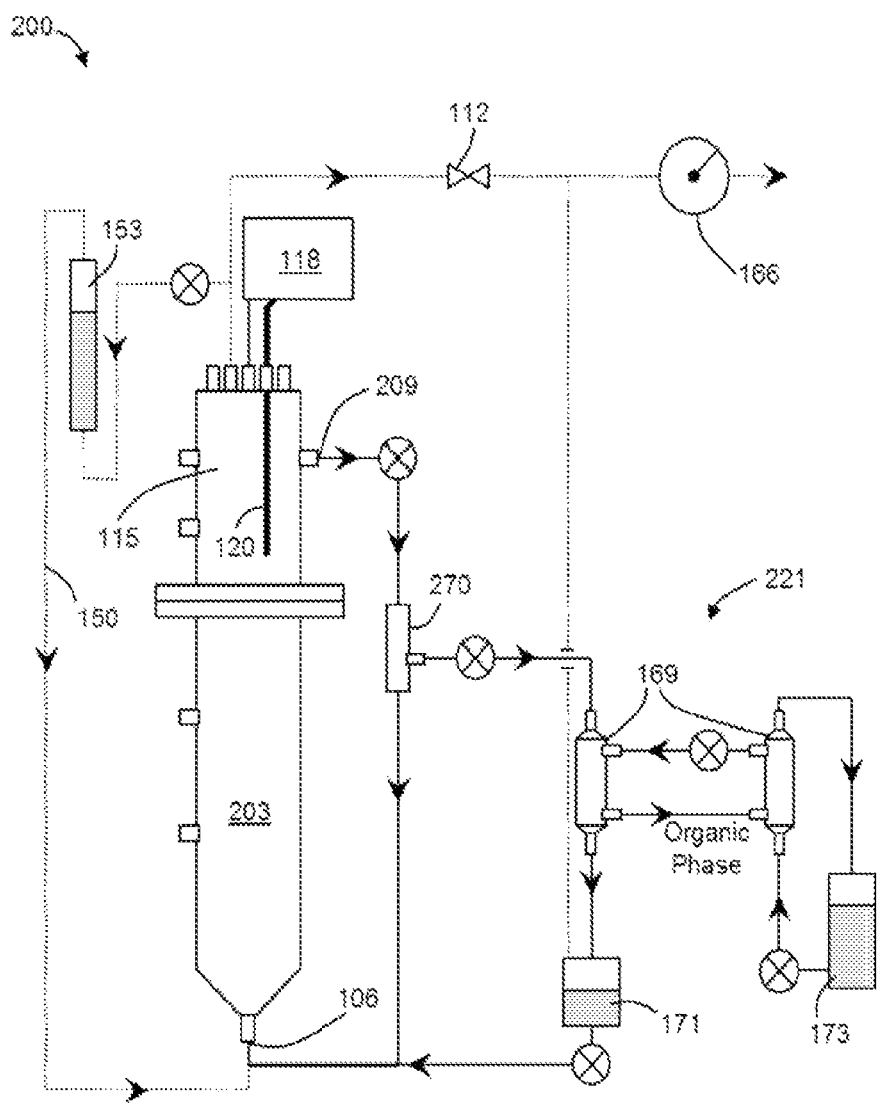
FIG. 2. Representative diagram of a system according to another embodiment of the present invention, wherein dotted lines depict gas conduits and solid lines depict liquid conduits.

The separation device 121 of the system 100 can be a membrane-based pertraction device, direct-contact liquid-liquid extraction device, membrane-based liquid-liquid pertraction device, on a solid-phase extraction matrix device, or with supported liquid membrane device, a stationary phase in an in-line column device, direct liquid/liquid solvent extraction device or supported liquid membrane device), electrochemical device, extraction through prevaporation device, and adsorption on an ion exchange media (e.g., ionic liquid) device. In one embodiment, the separation device 121 operates continuously. The separation device 121 may comprise hollow fiber membranes 169. The reaction mixture may flow through a settling basin 163 and/or a filter 160 (for example, a 5 μm filter) before reaching the separation device 121 such that particulate matter may be removed. Particulate matter may include, for example, biomass inadvertently removed from the reactor with the reaction mixture. In this way, in embodiments of separation devices 121 utilizing membranes, obstruction of the separation device 121 by particulate matter can be reduced or eliminated. In the embodiment of FIG. 2, a tangential flow filter 270 is utilized.

The pH controller 118 can comprise a pH probe 120 which can be positioned to monitor the pH of the reaction mixture. The pH controller 118 can be one in which the pH can be controlled by measuring the pH and adjusting the pH accordingly through addition of acid or base.

The remainder fluid is the fluid returning to the vessel 103 from the separation device 121. In one embodiment, the reminder fluid comprises $C_2$ to $C_8$ carboxylates where substantially all of the $C_6$ carboxylates have been removed by the separation device 121. In one embodiment, the remainder fluid comprises $C_2$ to $C_8$ carboxylates where substantially all of the $C_8$ carboxylates have been removed by the separation device 121. In another embodiment, the remainder fluid comprises $C_2$ to $C_8$ carboxylates where substantially all of the $C_6$ and $C_8$ carboxylates have been removed by the separation device 121. By "substantially all," what is meant is that at least 90%, 95%, 96%, 97%, 98%, or 99% of the desired carboxylate is removed by the separation device 121. In one embodiment, there is no detectable amount of desired carboxylate in the remainder fluid. The carboxylate can be detected, for example, by gas chromatography (GC).

The system 100 can further include a gas collection device (not shown) and/or gas recycling circuit 150. In the embodiment depicted in FIG. 2, a system 200 can also include a $CO_2$ scrubbing device 253. These devices can be in direct or indirect pneumatic communication with the headspace 115, 215 of the vessel 103, 203.

Carboxylates are used widely as chemical precursors in industry because they can be converted to many products such as esters, alcohols, and aldehydes and are also commonly used as microbial inhibitors. Production of methane is useful as it can be burned for heating or used to generate electricity.

The following examples are presented to illustrate the present invention. They are not intended to be limiting in any manner

EXAMPLE 1

Figure 3:
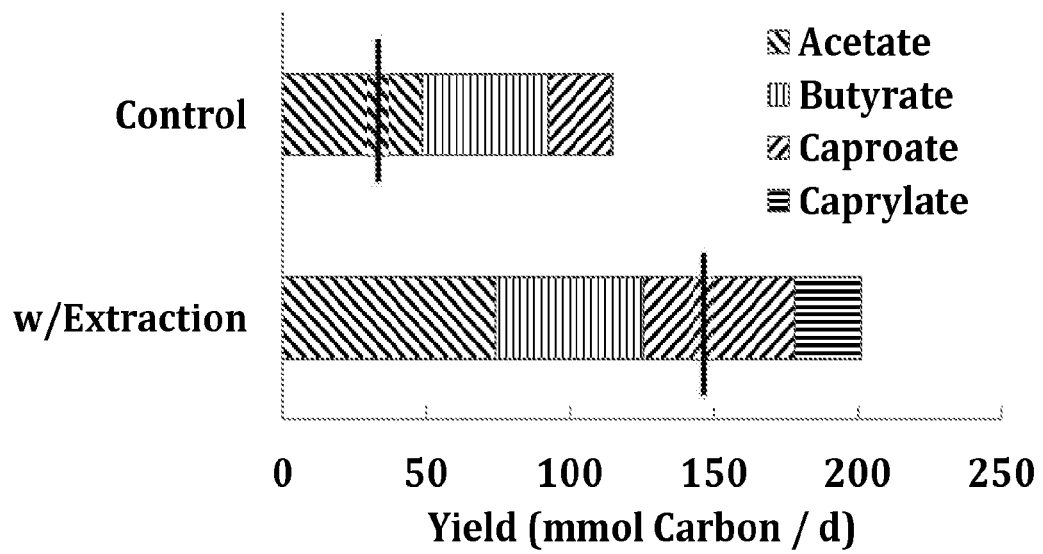
FIG. 3. Yield of carbon as carboxylate products in reactors fed dilute-acid pretreated corn fiber and ethanol with and without product pertraction.

Two bioreactors were operated with communities under anaerobic conditions to convert using ethanol and dilute-acid pretreated corn fiber. FIG. 3 shows the yield of carbon as carboxylate products in reactors fed dilute acid pretreated corn fiber (1.01 g VS/L/d) and ethanol (162.8 mmol Carbon/d). The control reactor did not include in-situ product pertraction while the reactor with extraction had 1 m$^2$ membrane surface to contact the organic phase. The line indicates the amount of the carbon in the fed ethanol that was utilized in each reactor. Odd-carbon chain carboxylates and caprate (C10) are also produced due to elongation of propionate and caprylate, respectively, but they are not shown here.

Figure 4:
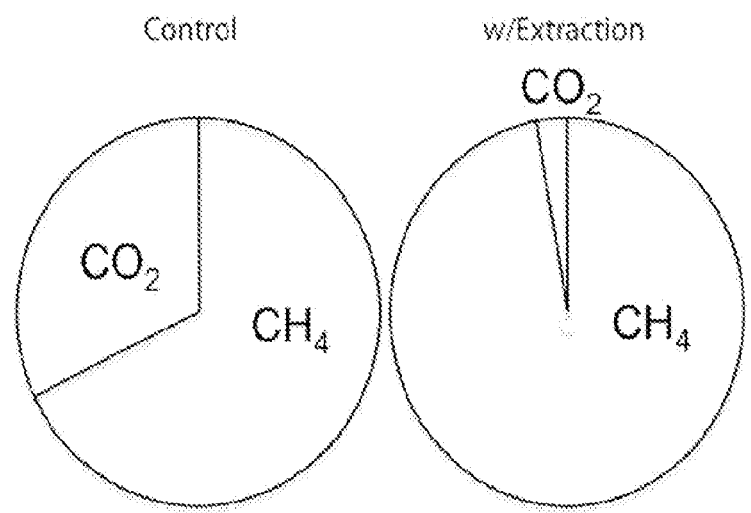
FIG. 4. Fraction of carbon in the biogas as methane and carbon dioxide in reactors fed dilute-acid pretreated corn fiber and ethanol with and without product pertraction.

The fraction of carbon in the biogas as methane and carbon dioxide in reactors fed dilute acid pretreated corn fiber (1.01 g VS/L/d) and ethanol (162.8 mmol carbon/d) is shown in FIG. 4. The control reactor did not include in-situ product pertraction while the reactor with extraction had 1 m$^2$ membrane surface to contact the organic phase.

EXAMPLE 2

This example demonstrates the production of $C_6$ and $C_8$ carboxylates. Two bioreactors were operated with communities under anaerobic conditions to convert ethanol and dilute-acid pretreated corn fiber to primarily n-caproate and n-caprylate. Promising chain elongation rates were achieved if both electron pushing (addition of ethanol as an external chemical source of energy and electrons) and in-situ product extraction (continuous removal of hydrophobic and acidic end products) were applied. Indeed, the n-caproate/n-caprylate carboxylate specificity (i.e., the ratio of n-caproate and n-caprylate in COD to all other fermentation products in COD) improved from 12% at 55° C. to 52% at 30° C. in the bioreactor with in-situ extraction and from 6% to 18% in the bioreactor without in-situ extraction.

In the vessel were microorganisms derived from inoculum or those that enter in the substrate, undegraded substrate (biomass and ethanol), degraded substrate (sugars, small particles, etc), and products of reactions (carboxylates, alcohols). The substrate material was added continuously or periodically (continuous or batch process) as described above. The substrate amount was added in amounts specified by the size of the reactor and the desired hydraulic retention time (volume of reactor/hydraulic retention time=volume of substrate added per time).

The two bioreactors degrading pretreated corn fiber were operated and supplemented with ethanol to promote chain-elongation reactions that upgrade the product spectrum to higher-value n-caproate and n-caprylate. A functional metagenomic survey was combined with constrained ordination of 12 bioreactor samples to determine the dynamic effects of operation (three temperatures and product-specific extraction) on the function of bioreactors. Further, the taxonomic structure of chain-elongation genes were evaluated to gain insights into how the community performs the chain-elongation function at these conditions.

Two ethanol-supplemented anaerobic sequencing batch bioreactors (ASBRs) treating dilute-acid pretreated corn fiber were operated for 124 days to direct metabolism toward medium-chain carboxylates (n-caproate, and n-caprylate). Two strategies were employed to direct the community to produce primarily n-caproate and c-caprylate in the liquid fraction. First, ethanol was added to both bioreactors at a rate of 0.75 g l$^{-1}$ d$^{-1}$ to encourage chain-elongation of acetate and n-butyrate that was produced during primary fermentation to n-caproate and n-caprylate and to encourage reduction of carbon dioxide to methane. Second, in-situ product specific extraction of n-caproate and n-caprylate was performed in one bioreactor ($R_p$), while products only left the other bioreactor in the effluent ($R_c$). Both bioreactors were operated for ~119 days at a thermophilic temperature (55° C.) and a pH of 5.5 with supplemented ethanol. After operating at 55° C., the temperature was reduced to 40° C., and after 33 days the temperature was reduced to 30° C. to promote a microbial community structure more efficient at the desired chain-elongation reactions.

An in-line continuously recirculating membrane-based liquid/liquid extraction system was incorporated (FIGS. 1, 2). To ensure extraction specificity, the system was designed to extract the more hydrophobic carboxylates (medium-chain) by employing a light mineral oil based solvent with 3% tri-n-octylphosphine oxide as a "carrier" molecule (Sigma-Aldrich, Inc). Further, only acidic molecules could be extracted by regenerating the solvent with a borate buffer solution maintained at pH=9 with automated addition of 5M NaOH. Thus, the driving force of extraction was the concentration gradient of undissociated acids while non-acidic molecules (e.g., ethanol) were not removed. To control for potentially negative effects of the solvent on the microbial community, both $R_p$ and $R_c$ were in contact with the solvent continuously. However, regeneration of the solvent only occurred for $R_p$, so carboxylates were not extracted from $R_c$ (FIG. 1). To provide a large aqueous/solvent contact area while maintaining separation of the phases, commercially available hollow-fiber membrane units were used, each providing ~0.5 m$^2$ of membrane surface area (Membrana, Inc). Two membrane units in series were located at the bioreactor broth/solvent interface and the solvent/aqueous alkaline interface. The bioreactor broth and aqueous alkaline solution were each continuously recirculated from the reservoir through the membrane and back at ~10 mL min$^{-1}$ The solvent was continuously recirculated between the bioreactor broth and aqueous alkaline regenerant. Noticeable reductions in extraction rates due to reduced solvent capacity were never experienced, and only replaced it when a leak occurred.

The chemical oxygen demand (COD) and volatile and total solids (VS and TS) levels in the substrate and effluent weekly or bi-weekly during the operating period were monitored, according to *Standard Methods* [APHA, 1998]. Every day the biogas production was measured and recorded the temperature and pressure to standardize the measurements. Biogas composition was measured weekly. For hydrogen composition a Gow-Mac Series 580 GC (Gow-Mac, Inc) with a 5'×¼" stainless column packed with 60/80 Carboxen 1000 packing material (Supelco, Inc) was used. The temperature of the column, injector, and detector were 100, 110, and 105° C., respectively, and the current to the TCD detector was 70 mA. Carbon dioxide and methane were measured with an SRI 8610C GC with a 1 m×¼" Rt-XLSulfur column (Restek, Inc). The temperature of the column, injector, and detector were 40° C., 25° C., and 101° C., respectively, and the current was 167 mA. The composition of the effluent and the stripping solution were determined by measuring the individual carboxylate and ethanol concentration after every 48-h cycle of feeding. Individual carboxylates were measured with an HP 5890 Series II GC equipped with an autosampler with a 15 m×0.53 mm Nukol column. Ethanol was measured with the same GC setup and a Supelco 6' ¼"×2 mm glass column packed with 10% CW-20M (treated with 0.01% $H_3PO_4$) on 80/100 Chromasorb WAW support.

Biomass was collected directly from bioreactors by mixing them for 5 min, rapidly sampling, centrifuging 2-mL vials of sample at 10,000 rpm for 10 min, disposing of supernatant, then freezing at −80° C. until further analysis. Whole community genomic DNA (gDNA) was isolated from 12 bioreactor biomass samples (4 from R1 and 8 from R2) with the MoBio PowerSoil DNA Isolation Kit (MoBio, Inc). DNA extraction from samples from 55° C. and 40° C. operation periods resulted in low levels of DNA, so DNA was concentrated by ethanol precipitation so that all samples had at least 10 ng/ul, measured with the PicoGreen dsDNA measurement kit (Invitrogen, Inc). Samples were sequenced with an Illumina HiSeq 2000 sequencing system in two lanes (6 samples in each lane), resulting in 10-15 million high quality and nonredundant reads per sample. The sequences were filtered for quality, using a trimming threshold of two consecutive low-quality bases, no unknown bases, and a final minimum length of 75 bp, and removal of identical sequences, using the QIIME 1.3.0 pipeline, and uploaded them to MG-RAST for further analysis.

Sequencing reads in MG-RAST were annotated based on SEED subsystem-based functional abundances, with a minimum 50% identity and an e-value cutoff of $1\times10^{-3}$. Next, a QIIME-style table was created using subsystem-based functions instead of OTUs so between-sample Pearson distances could be calculated to compare gene functional profiles. Pearson distances were calculated based on a table generated from the mean of 100 rarefactions at a depth of 1 million sequences per sample. Principal coordinates of the subsystem-based Pearson distances were generated to visualize the relatedness of sample metagenome structures. ANOVA in the QIIME package was used to determine genes that shifted in abundance with statistical significance ($p<0.05$ with a 3-fold abundance shift) between the operational categories temperature (55° C. vs. 30° C.) and extraction (extraction/no extraction).

To evaluate how operational or performance gradients described the subsystem-based function of the metagenome, redundancy analysis of the Pearson distance principal coordinates was used in the Vegan community ecology package for R. Redundancy analysis is essentially a principal component decomposition of principal coordinates. The resulting principal components are known as "unconstrained principal components", and they show as much separation as possible between samples on two axes. Constrained principal components are made by using gradients, such as operation or performance variables, to recreate the unconstrained principal components. Thus, in using subsystem-based between-sample distances, a good correlation between constrained and unconstrained axes indicates that the constraining variables are predictive of the subsystem-based function of the metagenome. Next, the entire set of principal coordinates was constrained by one operation or performance variable at a time and plotted them against one another (operation vs. performance). The type of correlation between the constraints is useful in identifying the dynamic between operation-explained metagenome functional composition and performance-explained functional composition, thus linking the operation and performance through the community metagenome.

USEARCH version 4.2.133 was used to search against the NCBInr database, which was divided into 29 equal parts to increase the speed of searches. Four million sequence reads were queried against each part of the database with a $10^{-6}$ e-value cutoff and 70% sequence identity (USEARCH does not count gaps, so this corresponds to ~60% identity in a BLAST search). A last common ancestor (LCA) algorithm was used to annotate the taxonomy and function of genes. After annotation, the taxonomy results were summarized for the whole metagenome and two processes within the metagenome: 1. The chain-elongation pathway catalyzed by *Clostridium kluyveri*, and 2. Both the NAD- and NADP-dependent alcohol dehydrogenases (EC 1.1.1.1 and EC 1.1.1.2).

Figure 5:
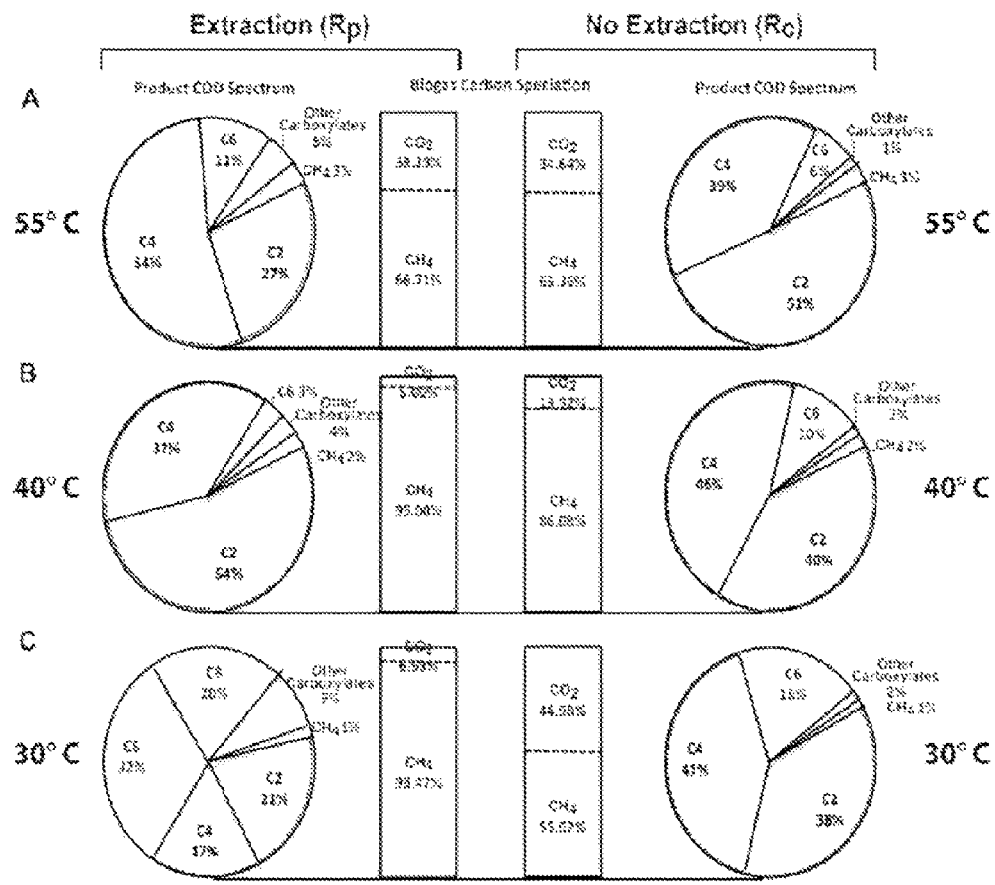
FIG. 5. Representative performance comparison between a bioreactor with in-situ product specific extraction ($R_p$) and a bioreactor without product extraction ($R_c$). A. Fermentation product specificities in chemical oxygen demand (COD) and biogas carbon speciation at 55° C.; B. Fermentation product specificities COD biogas carbon speciation at 40° C.; and C. Fermentation product specificities COD speciation and biogas carbon speciation at 30° C.

Two ethanol-supplemented anaerobic bioreactors converting dilute-acid pretreated corn fiber to carboxylates were operated. Ethanol (i.e., electron pushing) was supplemented as a source of energy and electrons for microorganisms that couple ethanol oxidation to reduction of short-chain carboxylates (acetate and n-butyrate), resulting in medium chain carboxylates (n-caproate and n-caprylate). Performance between a bioreactor with in-situ product specific extraction ($R_p$) and one without extraction ($R_c$) were compared at three different operating temperatures to optimize the chain elongation reactions leading to n-caproate and n-caprylate (FIG. 5). Here, n-caproate/n-caprylate product specificity (i.e., the ratio of n-caproate and n-caprylate in COD to all other carboxylates in COD) and carboxylate production rates (i.e., the rate of formation of a carboxylate or a group of carboxylates in COD) as the total of products collected in the effluent and in the extraction system were reported.

Figure 6:
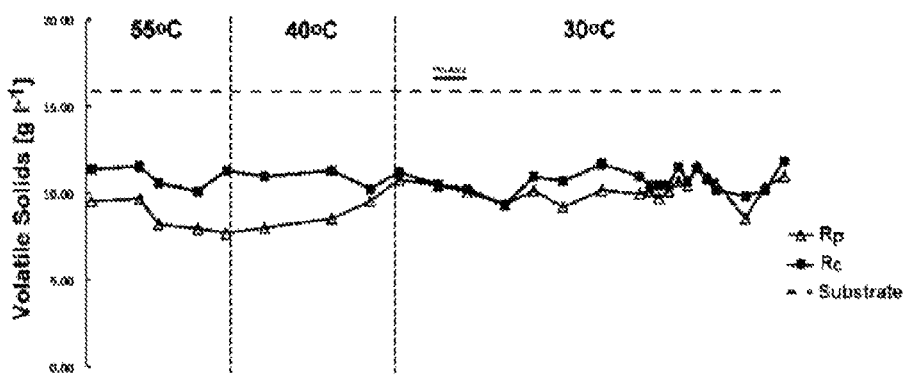
FIG. 6. An example of volatile solids (VS) removal in $R_p$ and $R_c$ during bioreactor operation at three temperatures. The dotted line indicates the concentration of VS in the dilute-acid pretreated substrate fed to both bioreactors.

The first operating condition tested was 55° C., corresponding to typical thermophilic bioreactor conditions. At this temperature, the n-caproate/n-caprylate product specificity was 11% and 6% for $R_p$ and $R_c$, respectively, (FIG. 5A) and about two-thirds of the biogas carbon was in methane. To promote chain elongation in the bioreactors, the temperature was decreased to 40° C., but the n-caproate/n-caprylate product specificity only changed marginally, indicating that this temperature was still not optimum for chain elongation (FIG. 5B). Carbon dioxide reduction to methane was more complete, with 95% and 85% of biogas carbon as methane for $R_p$ and $R_c$, respectively (FIG. 5B). Finally, the bioreactor temperature was decreased to 30° C., resulting in the maximum n-caproate/n-caprylate product specificity for $R_p$ of 52% and for $R_c$ of 18% (FIG. 5C). The n-caproate/n-caprylate production rate was six times higher in $R_p$ compared to $R_c$ (1.16 vs. 0.19 g COD l of bioreactor$^{-1}$ d$^{-1}$) and the total carboxylate production rate (i.e., the combined rate of formation of acetate, propionate, isobutyrate, n-butyrate, isovalerate, n-valerate, n-caproate and n-caprylate in COD) in $R_p$ was more than double that of $R_c$ (2.10 vs. 0.97 g COD l$^{-1}$ d$^{-1}$). Hydrolysis of the corn fiber substrate was relatively consistent throughout the entire operating period (FIG. 6), however, so the increase in specificity and product rates was due to higher rates of ethanol utilization in $R_p$. The portion of carbon as methane in the biogas at 30° C. was also higher in $R_p$ with 95% methane compared to 55% in $R_c$ (FIG. 5C). For $R_c$, this represented a decrease in methane production compared to 40° C., which can be attributed to accumulation of toxic n-caproate concentrations in the bioreactor.

The community metagenome structure of $R_p$ and $R_c$ was used to understand the dynamics between operational conditions and bioreactor utilization of the electron-pushing substrate ethanol to upgrade acetate and n-butyrate to n-caproate and n-caprylate and to reduce carbon dioxide to methane. The metagenome of a total of 12 samples (8 from $R_p$ and 4 from $R_c$) were sequenced; one sample from each bioreactor was collected at 55° C., one from each at 40° C., and 6 from $R_p$ and two from $R_c$ at 30° C. The 30° C. samples were collected at various levels of n-caproate/n-caprylate product specificity so that changes in the structure along performance gradients could be evaluated. Using barcoded sequencing on the Illumina HiSeq platform, an average of 12.5 million high-quality reads sample$^{-1}$ were obtained (average 98.2 bp seq$^{-1}$) after filtering. The primary measure of community metagenome structure was principal coordinates analysis of SEED subsystem-based functional abundances, using Pearson distances to compare gene functional profiles between samples. In redundancy analysis of the functional subsystem-based principal coordinates, 85% of community metagenome inertia (i.e., variation) on two axes (FIG. 7A) were visualized.

Figure 7:
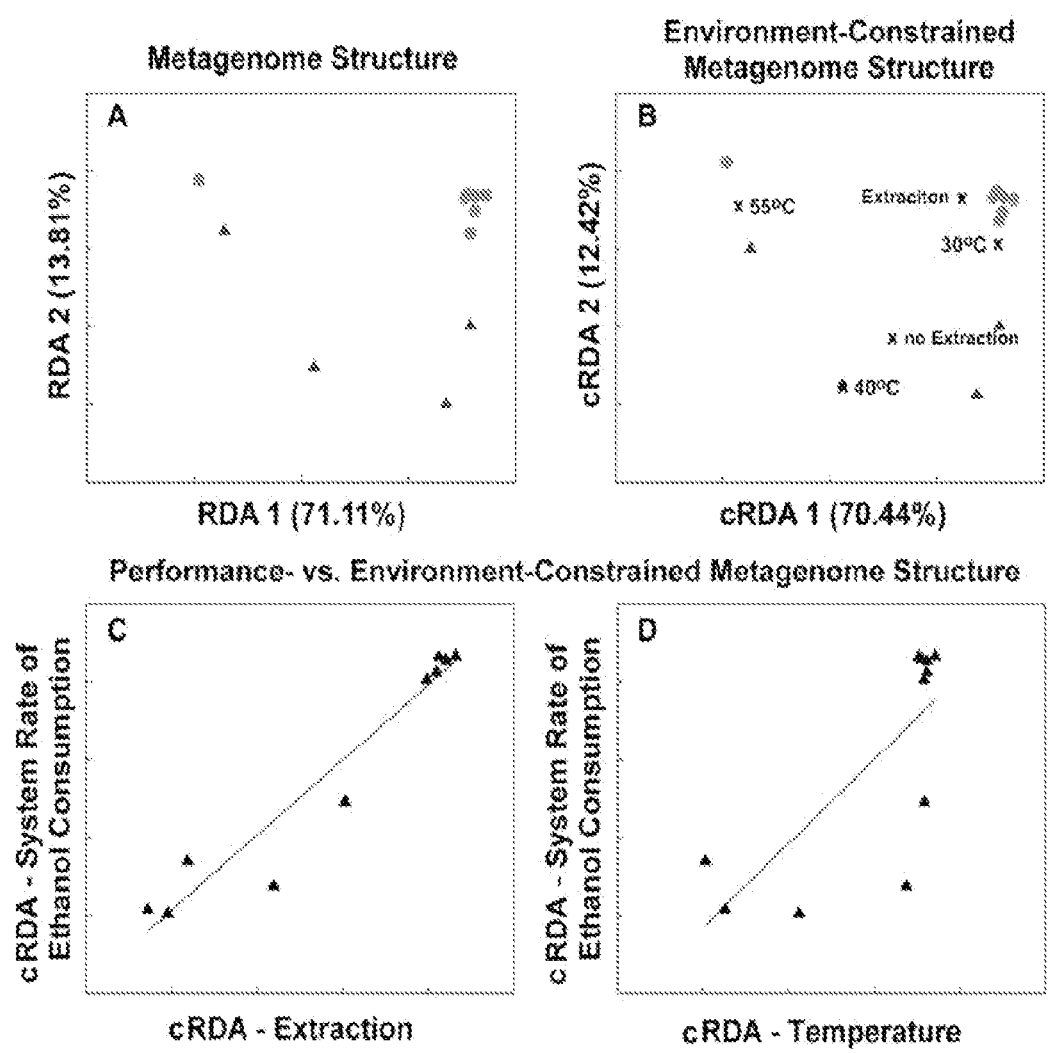
FIG. 7. Representative (constrained) redundancy analysis of SEED subsystem-based functional abundance principal coordinates. A. Unconstrained redundancy analysis showing as much of the functional abundance-based distance between samples as possible on two axes; B. The operational categories temperature and extraction predict ~98% of the unconstrained functional abundance-based distance between samples; C. One-dimensional constrained redundancy analysis comparison of the constraints rate of ethanol consumption (performance) and extraction (operation) display a linear dynamic relationship between the variables; and D. One-dimensional constrained redundancy analysis comparison of the constraints rate of ethanol consumption (performance) and temperature (operation) display a nonlinear dynamic relationship between the variables.

To find statistical correlation between operation, metagenome functional composition, and performance, constrained ordination of the functional subsystem-based principal coordinates was performed. The distances between samples were constrained with the operational variables temperature (55° C., 40° C., and 30° C.) and extraction (extraction or no extraction), and found that the variables described 98% of the inertia described by the metagenomic functional data (98% is calculated by the total inertia described by cRDA 1 and cRDA 2 divided by the total intertia described by RDA1 and RDA 2, multiplied by 100)(FIG. 7B). Next, to link bioreactor performance and metagenomic functional shifts due to operation, the functional subsystem-based principal coordinates were again constrained with three variables one at a time: 1. rate of ethanol consumption (performance), 2. temperature (operation), and 3. extraction (operation). n-Caproate, n-caprylate, and methane production in the systems all depended on ethanol, and therefore the rate of ethanol consumption describes the sum of electron pushing pathways that were active. Each of the operational-constrained axes were plotted against the performance-constrained axis (FIGS. 7C and 7D), and found that the aspects of metagenome functional composition that were determined by the bioreactor operation also explained bioreactor performance ($R^2=0.56$ for temperature and $R^2=0.93$ for extraction FIGS. 7C and 7D), although the relationships were different (nonlinear for temperature and linear for extraction). The nonlinear relationship for temperature explains that the community metagenome was capable of efficient ethanol utilization at 30° C. The linear correlation for extraction and performance indicates that extraction continuously altered the same metagenome functional composition that corresponded to performance. Thus, extraction efficiency is directly correlated to performance improvements.

Figure 8:
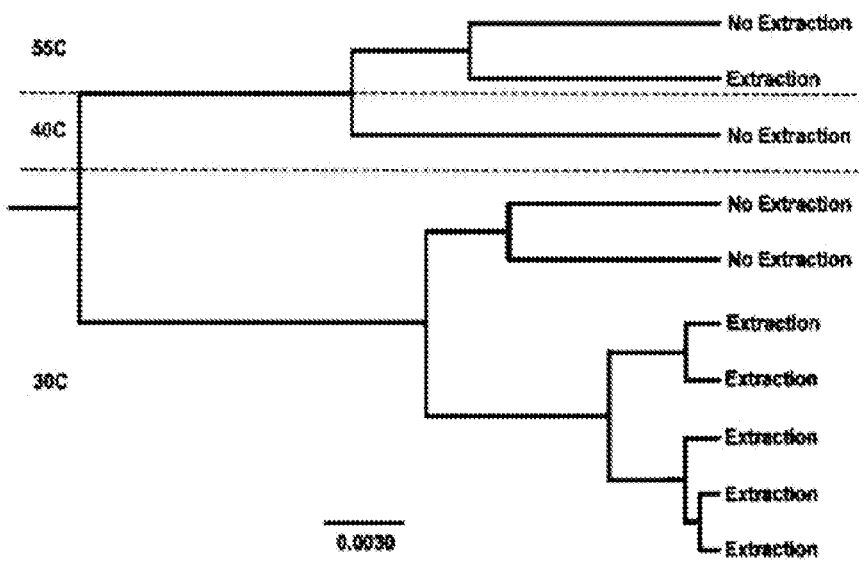
FIG. 8. Representative 100-fold bootstrapped sample-distance tree of the SEED subsystem-based functional abundance data (bootstrap values at all nodes is 1.0), demonstrating sample clustering first based on temperature, then based on extraction or no extraction. The pair of samples marked with an * represent samples with the highest n-caproate/n-caprylate specificity.

To further validate the inference that operation dictated the metagenomic functional composition and that the functional composition was indicative of performance, a 100-fold bootstrapped sample-distance tree was created of the same subsystem abundance data (again using Pearson distances). In the bootstrapped tree, bioreactor samples clustered by temperature, regardless of whether or not extraction was performed on the sample. Within the group of 30° C. samples, clustering was by whether the sample derived from $R_p$ (extraction) or $R_c$ (no extraction) (FIG. 8). Furthermore, within the group of extraction samples at 30° C., samples corresponding to the highest n-caproate/n-caprylate specificity clustered closely together (FIG. 8). Gene plots describing the significance of changes in gene abundance due to temperature or extraction further substantiated the fact that temperature had the largest effect on the community metagenome structure (529 significant genes at $p<0.05$ and a 3-fold relative abundance shift) followed by extraction (101 genes at $p<0.05$ and a 3-fold relative abundance shift). Therefore, the bioreactor operation determined the metagenome function of the microbial communities, which in turn, determined the ability of the community to accept ethanol as an electron pushing substrate.

The community metagenome functional composition could predict the ability of the bioreactors to accept ethanol as an electron-pushing substrate. Annotation of short shotgun-genome sequences with the taxonomy should be done with caution because the results are biased by both the database and the level of conservation of specific genes. Thus, NCBInr, a relatively large database of gene taxonomy was searched against, and used an LCA algorithm to assign genes with hits to multiple organisms to the last common ancestor of the multiple hits. Even with these strategies, significant bias in gene taxonomy results were expected, but performed the analysis only as a tool to form hypotheses. First, the distribution of taxonomy was examined for genes assigned to the class Clostridia in the entire metagenome of the samples (FIG. 9A), because *Clostridium kluyveri* or a similar organism was expected to perform the chain elongation reactions. From this analysis, it was apparent that the overall taxonomic distribution was primarily affected by temperature, with a large shift within Clostridia from primarily genes assigned to Thermoanaerobacterales to primarily genes assigned to Clostridiales. Abundance of any Clostridia taxonomic groups were not able to be directly correlated with n-caproate/n-caprylate specificity.

Figure 10:
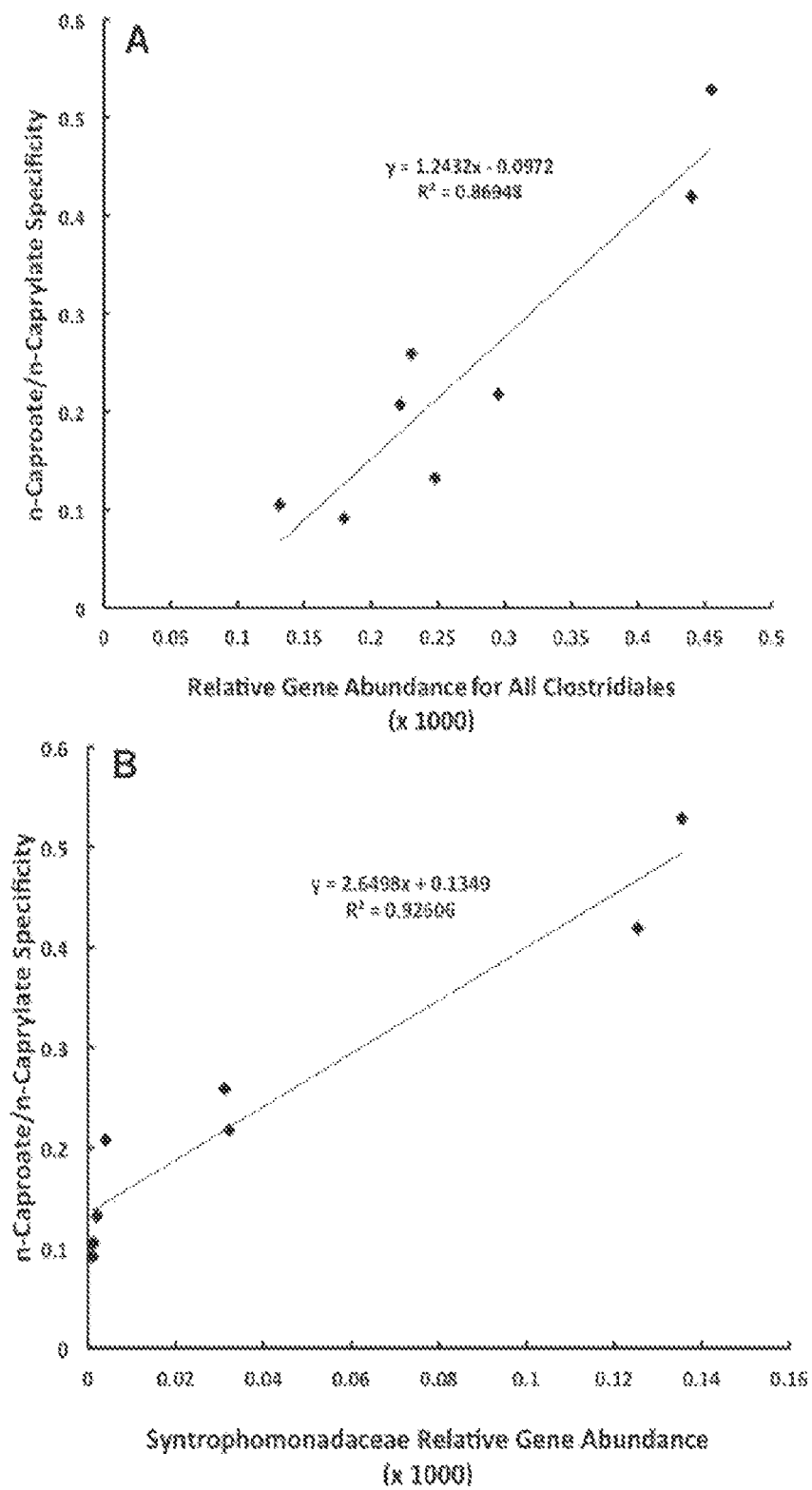
FIG. 10. Representative correlations between taxonomy of the chain-elongation genes and the n-caproate/n-caprylate product specificity. A. n-Caproate/n-caprylate product specificity vs. relative gene abundance (×1000) for all Clostridiales ($R^2$=0.87); and B. n-Caproate/n-caprylate product specificity vs. *Syntrophomonadaceae* relative gene abundance ($R^2$=0.93).

Next, the taxonomic distribution for only the metabolic pathway that *Clostridium kluyveri* uses to elongate acetate to produce n-butyrate (the same or analogous genes are used to produce n-caproate) was examined. In samples with the highest n-caproate/n-caprylate specificity, 65-75% of genes were assigned to the class Clostridia. Genes assigned to the family *Clostridiaceae* (which includes *Clostridium kluyveri*) were decreasing during the operating period at 30° C.; note that *Clostridium kluyveri* has already been implicated in chain elongation with ethanol in undefined mixed culture fermentations at pH 7. Two correlations to n-caproate/n-caprylate specificity at 30° C. were found: the entire order Clostridiales ($R^2=0.87$) and the family *Syntrophomonadaceae* ($R^2=0.93$) (FIG. 10). Bacteria in *Syntrophomonadaceae* (e.g., *Syntrophomonas wolfei*) are typically found in syntrophic relationships with hydrogenotrophs in anaerobic digesters, where they oxidize caroboxylates. It was not expected that this was its role in these chain-elongating bioreactors for two reasons. First, *Syntrophomonas* sp. oxidation reactions are inhibited by minor buildup of carboxylates (~20 mM acetate) and carboxylate levels in these bioreactors were much higher. Second, oxidation of n-butyrate at bulk bioreactor conditions was only marginally thermodynamically favorable at 30° C. ($\Delta G_r=-3$ kJ/mol to 0 kJ/mol), probably not enough to support growth. It is more likely that these Syntrophomonadaceae operated in a reductive fashion, similar to *Syntrophomonas wolfei* growth in pure culture on crotonate, wherein it uses an electron bifurcating pathway (oxidation of some of the crotonate for energy and reduction of some of the crotonate) similar to *Clostridium kluyveri* to produce n-butyrate and n-caproate.

Figure 9:
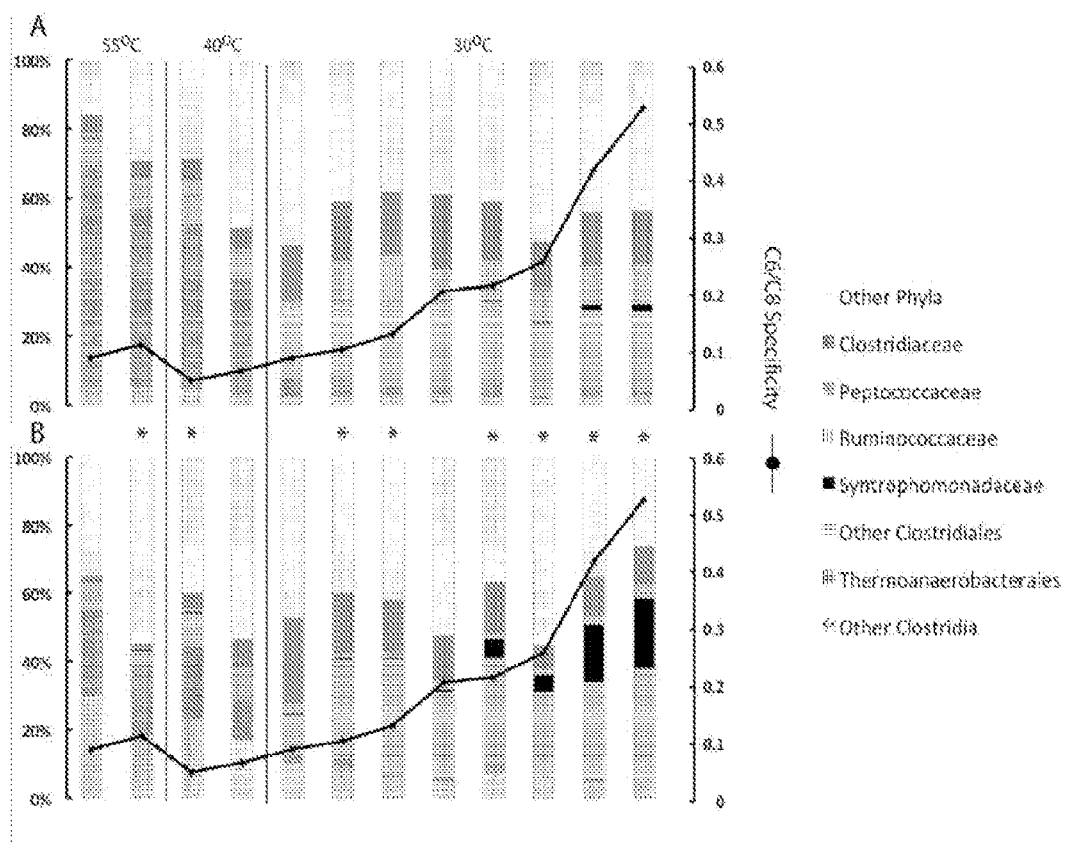
FIG. 9. Representative taxonomy distribution of the class Clostridia (other phyla are shown for comparison) in genes annotated by searching against the NCBI nr database, overlaid with the n-caproate ($C_6$)/n-caprylate ($C_8$) product specificity. Bars with a * symbol are samples taken from the bioreactor with in-situ product extraction ($R_p$). The bars are organized first by temperature (from left to right), then in order of increasing n-caproate/n-caprylate product specificity within temperatures. A. Taxonomic distribution within the class Clostridia for the entire metagenome. B. Taxonomic distribution within the class Clostridia for the chain elongation pathway from acetate to n-butyrate (pathway genes).

If a Syntrophomonadaceae sp. was partly responsible for chain elongation, it is surprising that relatively few genes were assigned to the family in the whole metagenome taxonomic distribution (FIG. 9A). However, other factors, such as poor specificity in taxonomic identification for Syntrophomonadaceae genome sequences, could obscure the population in the overall community.

Syntrophomonadaceae were correlated with n-caproate/n-caprylate specificity. Potentially, other organisms oxidized ethanol and Syntrophomonadaceae used an intermediate metabolite to produce n-caproate and n-caprylate. The taxonomic distribution of alcohol dehydrogenase genes in the bioreactors to determine how genes were distributed among groups of organisms was examined. The gene distribution for ethanol oxidation, compared to chain elongation, was much more distributed within bacteria. In the samples with the highest n-caproate/n-caprylate specificity, about 20-25% of ethanol oxidation genes belonged to various Clostridia, 5-15% belonged to Bacilli (mostly the family Lactobacillaceae), and 15-25% belonged to Actinobacteria (mostly the family Bifidobacteriaceae). Significant correlations to performance were not found. The wider distribution amongst taxa may indicate that several organisms were involved in ethanol oxidation. The oxidation could proceed either directly to acetate and hydrogen or by an unknown process that couples ethanol oxidation to formation of some intermediate compound, such as crotonate, which Syntrophomonadaceae can convert to n-caproate. At bulk conditions during operation at 30° C. in $R_p$, ethanol oxidation directly to acetate and hydrogen was thermodynamically favorable.

Only a few alcohol dehydrogenase genes were assigned to Archaea (not shown), indicating that a direct coupling of ethanol oxidation and carbon dioxide reduction by a single methanogen (e.g., *Methanogenium organophilum*) was unlikely. Therefore, hydrogen utilized for carbon dioxide reduction was produced when ethanol was oxidized, either directly to acetate and hydrogen, or with a coupling reaction such as chain elongation that also produced hydrogen.

It was determined via metagenomic analysis of carboxylate bioreactors that the operational variables temperature and extraction had significant effects on metagenomic functional composition of the bioreactors. In the bioreactors, temperature affected the functional metagenome content the most, which is expected because microbial colonization of diverse temperatures has required distinct evolutionary changes. The nonlinear (i.e., threshold) correlation of performance to the metagenome functional composition caused by temperature in the bioreactors indicates that 30° C. was the only temperature at which the bioreactor community metagenome could catalyze chain elongation with ethanol. Extraction was also important, and the linear correlation to performance through functional composition indicates that bioreactor metagenomes exhibited a smooth transition from no extraction and poor ability to utilize ethanol to extration and rapid ethanol utilization. Because the main function of extraction is to remove endproducts, the transition to communities allowing more electron pushing would continue along this gradient if product removal were more efficient.

It was found that supplementing ethanol to bioreactors converting dilute-acid pretreated corn fiber to carboxylates at 30° C. while simultaneously performing in-situ product-specific extraction adjusts the product spectrum from primarily acetate and n-butyrate to higher-value n-caproate and n-caprylate. Here, it was found that within genes in the chain elongation pathway, the taxonomy correlated with n-caproate/n-caprylate specificity was the family *Syntrophomonadaceae*. Because *Syntrophomonas* sp. are known to reduce crotonate to n-butyrate and n-caproate, and because bioreactor conditions made oxidation of short-chain carboxylates by these species unlikely, the results suggest that species within *Syntrophomonadaceae* may have participated in chain elongation. Further, alcohol dehydrogenase genes were dispersed throughout a wide variety of taxa, indicating that electrons may have been transferred between species. Thus, the results suggest that another bacterium may be required in a hitherto undescribed syntrophic relationship.

Based on the functional content of bioreactor metagenomes, it was determined with statistical certainty that effective electron pushing with ethanol is only possible at low temperature (30° C.) and with efficient product-specific extraction. This system resulted in up to 54% n-caproate/n-caprylate specificity and fermentation product rates of n-caproate/n-caprylate that were 6 times those without product specific extraction. The approach used combined relatively low-cost (~$250 per sample) metagenomic sequencing methods with ecological techniques to precisely determine the operation/performance relationship in bioreactors converting dilute-acid pretreated corn fiber to n-caproate and n-caprylate.

EXAMPLE 3

This example demonstrates chain elongation with reactor microbiomes.

Figure 11:
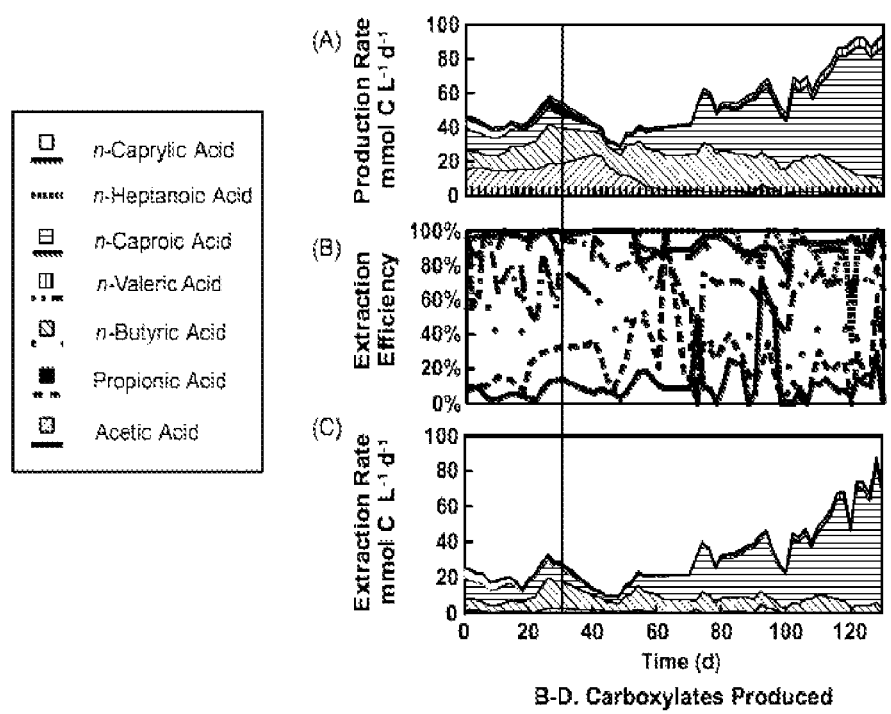
FIG. 11. Representation of effect of in-line extraction on production of carboxylic acids; A. Production rate of $C_2$-$C_8$ carboxylic acids over time; B. Extraction efficiency of $C_2$-$C_8$ carboxylic acids as the percentage of produced acid that was extracted over time; and C. Extraction rate of $C_2$-$C_8$ carboxylic acids over time. The vertical line in A-C represents the switch to real yeast-fermentation beer as substrate and an increase in extraction membrane surface area from 1 $m^2$ to 2 $m^2$.
Figure 12:
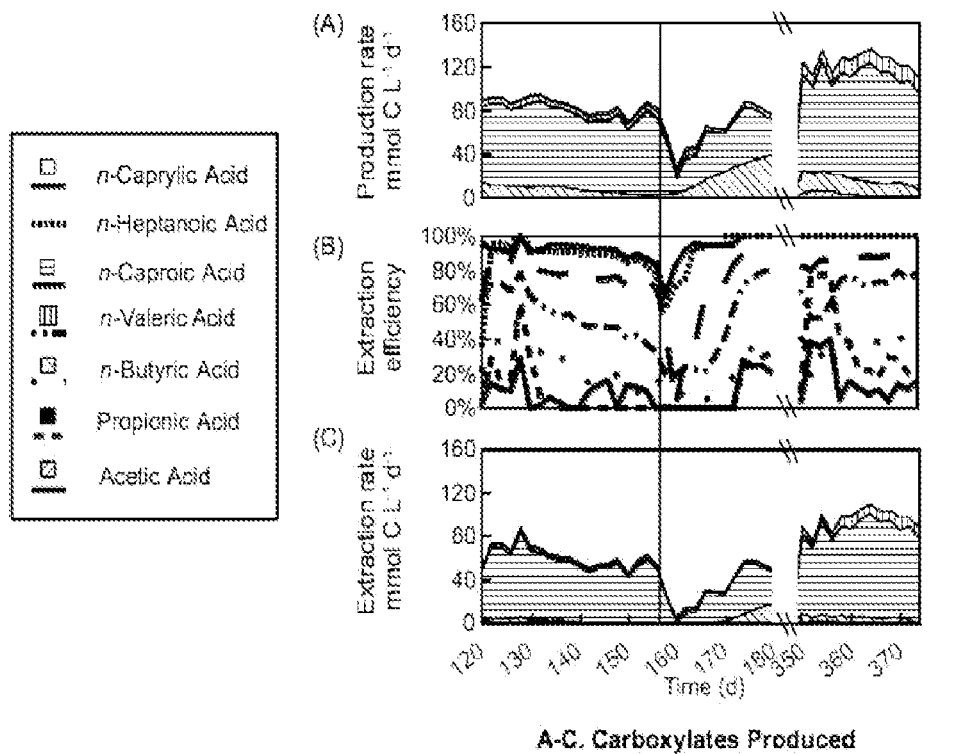
FIG. 12. Representative performance of the n-caproic acid producing bioreactor on days 120-180 and 350-374, including the effects of an extraction module failure on day 157, and the maximum n-caproic acid production rate on day 364 after extraction rates were increased on day 300 due to increasing the extraction membrane surface area 3.5 times. Days 120-130 correspond to the same days in FIG. 1: A. Production rate of $C_2$-$C_8$ carboxylic acids on days 120-180 and 350-374; B. Extraction efficiency of $C_2$-$C_8$ carboxylic acids as the percentage of produced acid that was extracted in-line; and C. Extraction rate of $C_2$-$C_8$ carboxylic acids is the rate of in-line recovery of each acid. The vertical line in A-C represents the failure of an extraction module on day 157. Performance data between days 180 and 350 was omitted to only focus on one membrane failure and the sustained production of n-caproic acid after installation of a new and larger extraction system on day 300. In the interim, problems arose from cracking membrane housing, and these problems disappeared after switching to stainless steel housing.
Figure 13:
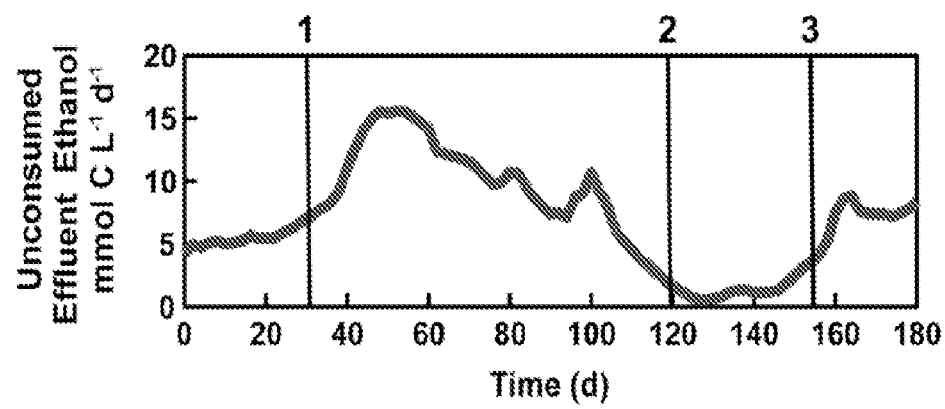
FIG. 13. Representative ethanol concentration in effluent of the n-caproic acid producing bioreactor. Ethanol in the effluent occurred when it was not oxidized during chain elongation. The vertical lines represent: 1. The switch to yeast fermentation beer substrate; 2. The HRT decrease from 15 days to 12 days, and 3. The failure of the extraction modules.

Materials and Methods: Bioreactor Setup and Operation. A 5-L glass bioreactor was operated for over a year to convert yeast fermentation beer to n-caproic acid (FIG. 11 and FIG. 12). The yeast fermentation beer was received in one shipment from Western New York Energy in Medina, N.Y. The raw, undiluted beer had a total and volatile solids content of 125.73±0.14 g $L^{-1}$ (n=6) and 117.19±0.15 g $L^{-1}$ (n=6), respectively, a chemical oxygen demand (COD) of 450.50±51.12 g $L^{-1}$ (n=6), and the ethanol content was 152.7±3.4 g $L^{-1}$ (~15%) (n=4). The beer was diluted 6.6 times before feeding to the bioreactor; in a real industrial setup, recycled liquor would have been used instead of make-up water. The bioreactor included a heated water jacket connected to a water heater to maintain a temperature of 30° C., an hourly automatic mixing system that worked by recirculating biogas with a peristaltic pump, and an automated pH control system, which pumped 5M NaOH or HCl during mixing to maintain a pH of 5.5 (range 5.4-5.6). To prevent under pressure in the bioreactor during effluent withdrawal and feeding, the headspace was connected to a device that equalized pressure with the room while preventing air intrusion. The bioreactor was fed semi-continuously on a 48-hour schedule: substrate was first fed into the bioreactor (time 0), followed by a react period with pH control, hourly mixing, and continuous n-caproic acid extraction (hours 0-47), followed by a 1-h biomass settling period (hour 47), and rapid effluent removal of a volume equal to substrate volume with a peristaltic pump (time 0). A hydraulic retention time (HRT) of 15 days was maintained (666 mL of substrate fed per cycle to the 5-L bioreactor) and a substrate organic loading rate of 4.5 g COD $L^{-1}$ $d^{-1}$ (ethanol loading rate: 66.6 mmol C $L^{-1}$ $d^{-1}$) through day 120. By day 120, chain-elongation reactions consumed nearly all available ethanol in the substrate (FIG. 13), and therefore the HRT was decreased to 12 days (833 mL of substrate per cycle for the 5-L bioreactor), resulting in a higher substrate loading rate of 5.7 g COD $L^{-1}$ $d^{-1}$ (ethanol loading rate: 83.3 mmol C $L^{-1}$ $d^{-1}$) for the remainder of the operating period. The bioreactor was inoculated from previously operating bioreactors optimized for n-butyric acid production from dilute-acid pretreated corn fiber. Originally the n-butyric acid-producing bioreactor was started with a natural microbiome from sheep rumen and a thermophilic anaerobic digester from the city of Duluth, Minn. (Western Lake Superior Sanitary District, Duluth, Minn.). For the first 30 days of the current study, the bioreactor was fed dilute-acid pretreated corn fiber, which was supplemented with ethanol at an HRT of 15 days and a loading rate of 1.7 g COD $L^{-1}$ $d^{-1}$ (ethanol loading rate: 32.6 mmol C $L^{-1}$ $d^{-1}$).

In-line Liquid/Liquid n-Caproic Acid Extraction. To prevent product inhibition and to recover the product, n-caproic acid was continuously extracted using a membrane-based liquid/liquid extraction system (FIG. 11). The extraction system consisted of hollow-fiber hydrophobic membrane contactors that allowed a high surface area for contact between the aqueous and solvent phases. Eight commercially available hydrophobic membranes with a contact area of 2.32 $m^2$ were used for both the bioreactor/solvent and solvent/stripping interfaces (four on each side) (1.5×5.5 MiniModule X50, Liqui-Cel, Membrana, Wuppertal, Germany). On day 300, the membrane contact area was increased for both the bioreactor/solvent and solvent/stripping interfaces to 8.1 $m^2$ to avoid limitations due to rate of product extraction (4×13 316L SS X50, Liqui-Cel, Membrana). Indeed, until the end of the study the substrate-feeding rate was limiting the production rate and not the extraction rate. The driving force for the extraction was two-fold: 1. A reactive solvent was used (3% tri-n-octylphosphineoxide in mineral oil, Sigma-Aldrich, St. Louis, Mo.), which is more selective for hydrophobic molecules, such as n-caproic acid, compared to shorter-chain molecules, such as acetic acid. A pH gradient was maintained to take advantage of the dissociation constant for n-carboxylic acids ($pK_a$=4.8-4.9) to selectively extract undissociated acids from the bioreactor at pH 5.5 and recover them in the dissociated form in a pH 9 aqueous solution. First, the bioreactor supernatant was pumped into the lumen side (inside the fibers) of the hollow-fiber membrane units at 10 mL/min after being filtered to remove remaining large particles (as much of the particles as possible were returned to the bioreactor on a weekly basis). The solvent, which wet the hydrophobic membranes, was pumped at the same rate on the shell side (outside the fibers) of the membrane, counter-flow to the bioreactor liquid. The solvent was constantly recirculated between contact with the bioreactor liquid and the shell side of a second membrane unit, where it contacted an aqueous phase buffered with a 0.5 M borate solution at pH 9. The pH 9 solution was continuously recirculated from a 5-L reservoir where a pH controller maintained the pH by automatic addition of 5M NaOH.

Methanogenic Activity Test. 35-mL batch fermentation vessels were operated in 93-h fermentations to test whether bioreactor microbiomes produced methane from acetic acid or only from carbon dioxide with hydrogen or ethanol as the source of reducing equivalents (electrons). All batch reactions were carried out in triplicate. Four triplicate sets of batch bottles were prepared (no source of electrons for methanogens). In short, in an anaerobic hood, 0.75 mL basal medium was added, ~8 mmol $g^{-1}$ VS acetic acid, ~4 mmol $g^{-1}$ VS n-butyric acid, and 100 mM 2-(N-morpholino) ethanesulfonic acid (MES) buffer to a total volume of 7.25 mL, added 0.25-mL inoculum and 0.1-mL sodium sulfide, corrected to pH 5.5 at 30° C. with NaOH (total volume ~10 mL), capped the bottles with butyl rubber stoppers and crimp caps, and flushed each bottle with nitrogen for 10 min (set A). To set B, also added was ~10 mmol $g^{-1}$ VS carbon dioxide and hydrogen; to set C, ~6 mmol $g^{-1}$ VS ethanol was added; and to set D, ~10 mmol $g^{-1}$ VS carbon dioxide and hydrogen and ~6 mmol $g^{-1}$ VS ethanol was added. The inoculum was collected from the well-mixed bioreactor before the substrate was changed from dilute-acid pretreated corn fiber to yeast fermentation beer on day 30. The headspace pressure was periodically measured in the batch bottles and analyzed headspace gas for methane, carbon dioxide, and hydrogen. The liquid substrates and the products ethanol, acetic acid, and n-butyric acid were measured at the time of inoculation and at the end of 93 h. At the end of the run, the volatile solids (VS) concentration was measured in each bottle to normalize the measurements for the amount of biomass in each batch bottle.

Chemical Analysis. All chemical analyses were performed on a regular schedule. At the end of each 48-h feeding cycle the biogas production was measured and recorded the temperature and pressure to standardize the measurements. Biogas composition was measured weekly. For hydrogen composition, a Gow-Mac Series 580 GC (Gow-Mac Instrument Co, Bethlehem, Pa.) with a 5'×¼" stainless column packed with 60/80 Carboxen 1000 packing material was used (Supelco, Sigma-Aldrich, St. Louis, Mo.). The temperature of the column, injector, and detector were 100° C., 110° C., and 105° C., respectively, and the current to the TCD detector was 70 mA. Carbon dioxide and methane were measured with an SRI 8610C GC with a 1 m×¼" Rt-XLSulfur column (Restek, Corp, Bellefonte, Pa.). The temperature of the column, injector, and detector were 40° C., 25° C., and 101° C., respectively, and the current was 167 mA. The composition of the effluent was determined and the stripping solution by measuring the individual carboxylic acids and ethanol concentration after every feeding cycle. Individual carboxylic acids were measured with an HP 5890 Series II GC (Hewlett-Packard, Palo Alto, Calif.) equipped with an autosampler with a 15 m×0.53 mm Nukol column. Ethanol was measured with the same GC setup and a Supelco 6' ¼"×2 mm glass column packed with 10% CW-20M (treated with 0.01% $H_3PO_4$) on 80/100 Chromasorb WAW support.

A nonsterile, 5-L bioreactor as inoculated with natural microbiomes and fed beer from the corn ethanol industry for months, while controlling the pH at 5.5 and the temperature at 30° C. (FIG. 1). An n-caproic acid production rate of 76.5 mmol C $L^{-1}$ $day^{-1}$ (1.5 g $L^{-1}$ $day^{-1}$) was achieved, which is similar to methane production with complex substrates in anaerobic digesters (an established bioenergy system with reactor microbiomes), and a product specificity of 79% (carbon in n-caproic acid compared to all fermentation products) (FIG. 11A). This performance was achieved by continuously removing n-caproic acid with liquid/liquid extraction, and was limited by extraction rates; an extraction system failure immediately decreased production, but the system recovered following repair of the extraction module (FIG. 12). Further, by increasing the extraction rate (after increasing the membrane surface area), a higher maximum n-caproic acid production rate of 108.3 mmol C $L^{-1}$ $day^{-1}$ (2.1 g $L^{-1}$ $day^{-1}$) was sustained (FIG. 12).

A pH gradient (5.5-9.0) was used as the driving force to specifically extract acidic product by diffusion through membranes. This is a low-energy extraction process, requiring energy only to pump bioreactor, solvent, and extraction solutions (FIG. 14A; supplementary methods). The solvent solution was 3% tri-n-octylphosphineoxide in mineral oil, which preferentially extracted hydrophobic molecules, resulting in extraction efficiencies of 83-93% for medium-chain carboxylic acids and 5-31% for short-chain carboxylic acids (FIG. 14C). The continuous extraction resulted in high specificity for recovering and concentrating n-caproate as a product (97%; FIG. 11C), representing 10% more carbon than was provided as ethanol.

Figure 14:
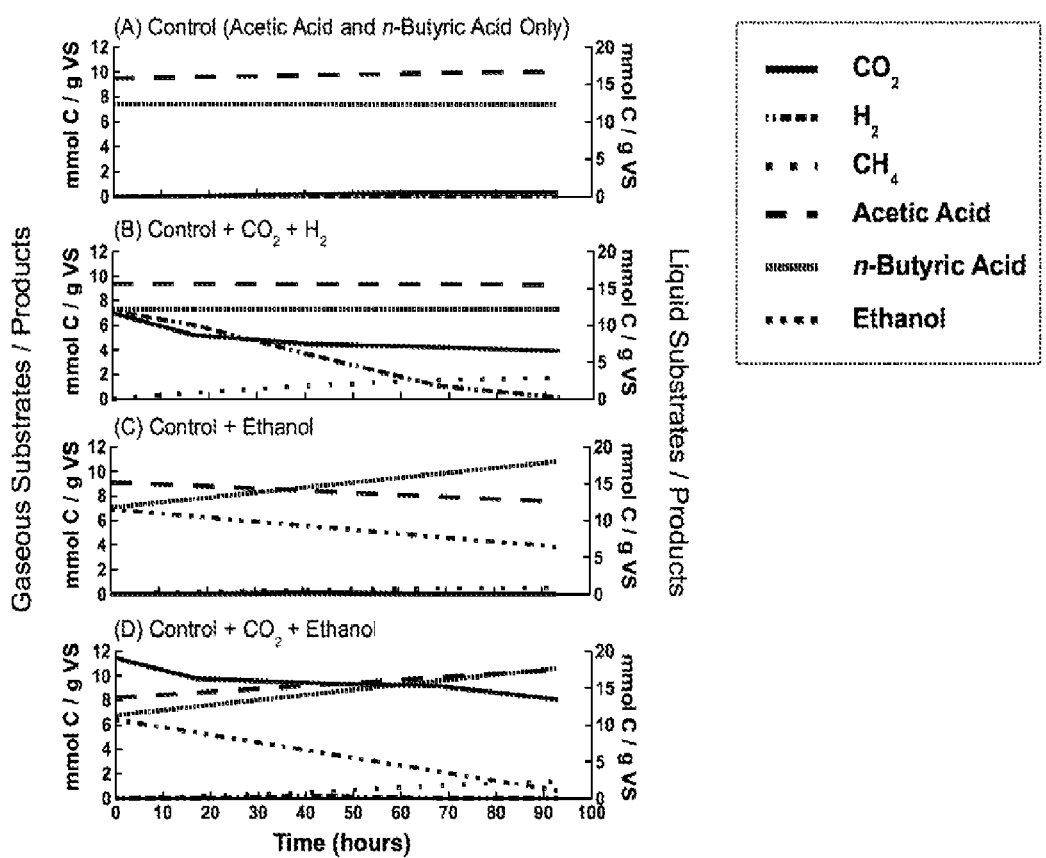
FIG. 14. A representative 93-h methanogenic activity test at pH 5.5 and 30° C. demonstrates that microbiomes did not produce methane from acetic acid but produced it from $CO_2$ with $H_2$ or ethanol as sources of reducing equivalents: A. Control set demonstrates that methane is not produced by microbiomes in the presence of acetic acid; B. The microbiome produces methane from $CO_2$ and $H_2$ but acetic acid is not consumed; C. By consuming ethanol, the microbiome elongates some of the acetic acid to n-butyric acid (n-caproic acid was not detected); and D. When $CO_2$ and ethanol are added, microbiomes consume most of the ethanol because acetic acid is elongated to n-butyric acid and $CO_2$ is reduced to $CH_4$. Despite acetic acid elongation, acetic acid concentrations increase because ethanol is oxidized to acetic acid either by methanogens or by other microbes, which transfer $H_2$ to methanogens.

In-line extraction of n-caproic acid and controlling the bioreactor pH at 5.5 resulted in simultaneous chain elongation and methanogenesis when methane is produced only from hydrogen and carbon dioxide and not from acetic acid (FIG. 14). Continuous extraction of the unionized n-caproic acid was necessary due to its microbial toxicity at a pH of 5.5 (close to its pKa of 4.88 at 30° C.). Carbon in the bioreactor off gas consisted of primarily methane (99.6%; 3% of fermentation product carbon); an advantageous coproduct compared to carbon dioxide.

Studies of community structure-function relationships showed that diverse anaerobic microbiota are stable and resilient, that the community structure dictates performance, and that operating conditions affect structure. These findings not only refute the claim that microbiomes are inefficient and unpredictable, but also suggest that they can be shaped for a specific function. Membership and function of microbiome samples were characterized over time using the: i. 454 titanium platform for 16S rRNA gene sequencing; and ii. Illumina platform for shotgun metagenomic sequencing (supplementary methods). An average of ~5,800 high-quality 16S rRNA gene sequences were generated per sample (n=7) from which 839 operational taxonomic units (OTUs; 97% ID) were picked and assigned taxonomy (supplementary methods). Five abundant OTUs that were significantly correlated (r>0.8 and p<0.05) were found with increasing n-caproic acid production rates (FIG. 15A and Table 1). Relative abundance of *C. kluyveri* reached 4% of the microbiome on day 120 of the operating period when chain elongation rates were high (FIGS. 14A and 18A), while other OTUs, including one from the family Ruminococcaceae, became important as well. A lower community richness (α diversity) and more uneven distribution of taxa within the microbiome (FIG. 15B) coincided with improvements in reactor performance.

Figure 15:
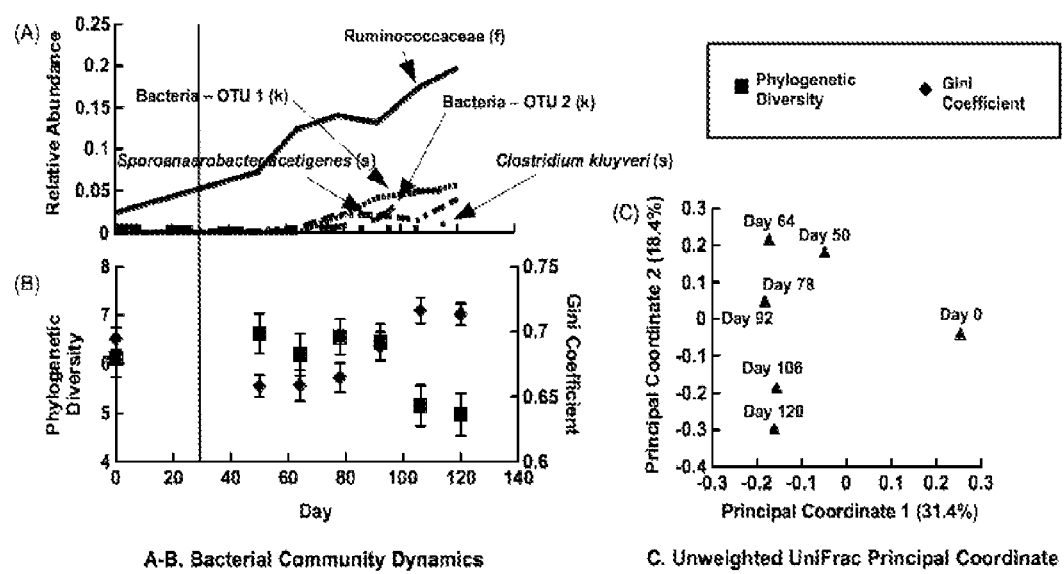
FIG. 15. Representative time-series analysis of the microbiome: A. Relative abundance vs. time of OTUs that were significantly (r>0.8) correlated with the rate of n-caproic acid production. OTU taxonomy was assigned to the most specific level possible with (k): kingdom, (f): family, and (s): species; B. α Diversity and evenness of samples (100 rarefactions of 500 reads per sample). Gini coefficient is a measure of community evenness where 0 is a perfectly even community with OTU abundance distributed and 1 is a perfectly uneven community for which only one OTU dominates; and C. β Diversity for which Unweighted UniFrac principal coordinates represent as much of the between-sample community phylogenetic variation as possible in two coordinates (49.8%). The line in a-b represents a switch to real yeast-fermentation beer and an increase in extraction membrane surface area.
Figure 16:
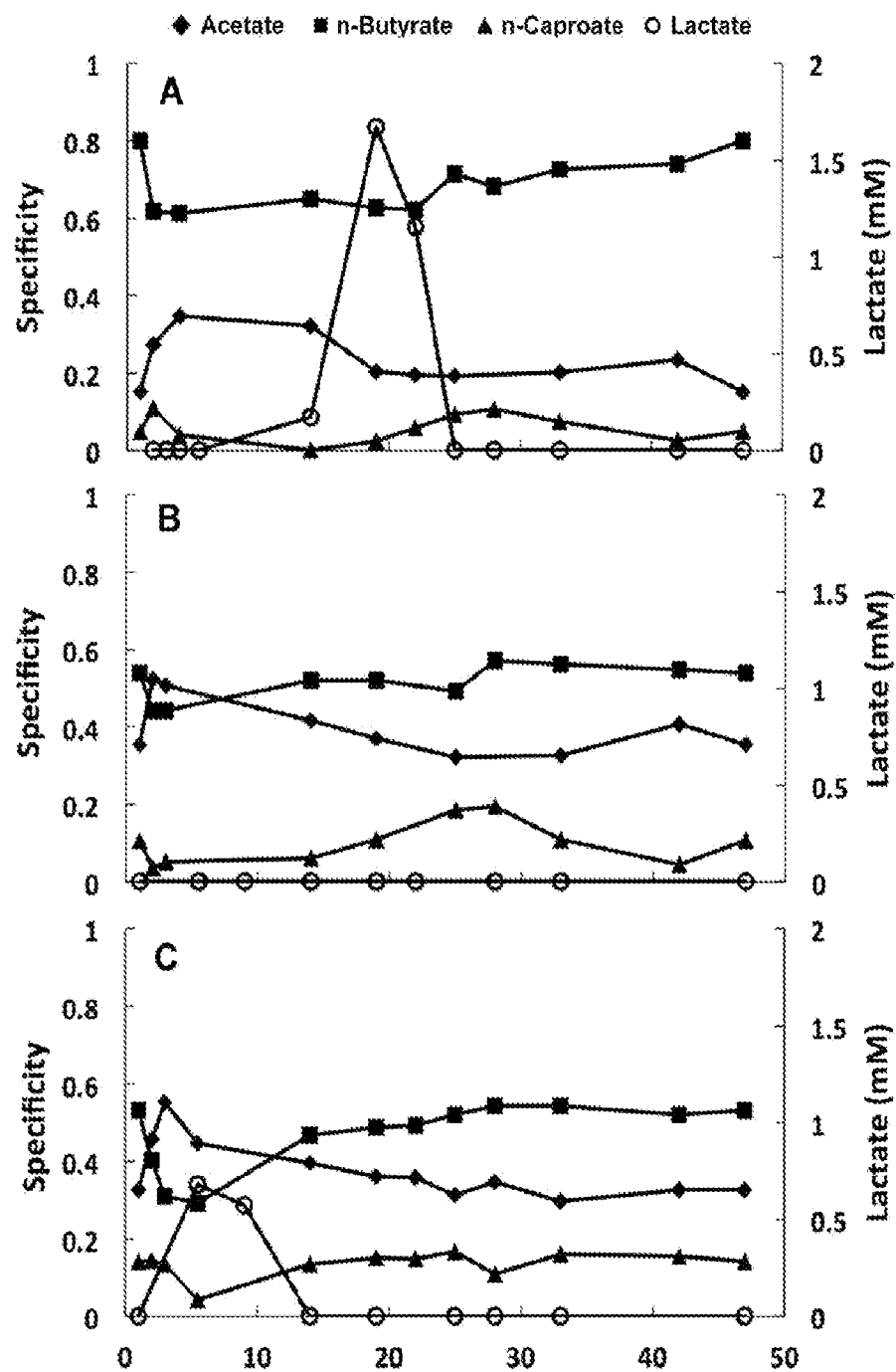
FIG. 16. A representative 48-hour cycle analysis demonstrates the dynamic relationship between intermediate lactate and the acetate, n-butyrate, or n-caproate specificities (i.e., ratio of specific product in COD to all fermentation products in COD) in Racid (A), Rbase (B), and Rheat (C).

The shotgun metagenomic analysis (~2.4 billion by per sample [n=10]) suggested that more than 50% of all assigned reads were from *Clostridium* spp., and that this genus dominated many of the major metabolic pathways (FIG. 15). Other genera, including *Ethanoligenens* (fam. Ruminococcaceae), *Bifidobacterium*, and *Desulfitobacterium*, represented important pools of genes for hydrolysis and ethanol oxidation (FIGS. 19 and 20). This explains why a Ruminococaceae OTU was correlated with n-caproic acid production (FIG. 15A). *Clostridium* spp. dominated the chain-elongation gene pool; however, *C. kluyveri* may not have been the only *Clostridium* sp. involved in carboxylic acid elongation because other phylogenetically diverse rumen isolates produce n-caproic acid from complex substrates.

The differentiation between microbiomes (β diversity) showed a clear time-series path during which production was elevated (FIG. 15C). This nonrandom behavior of the microbiome was identified as shaping, resulting from adaptation to: i. a pH of 5.5; ii. a temperature of 30° C.; iii. feeding a reduced compound (ethanol [FIG. 13]) together with organic compounds; and iv. extracting the product continuously and selectively. In other words, the tools to control the reactor microbome to generate primarily the products wanted have been achieved. The chain-elongation rate of the shaped microbiome is comparable with pure cultures of *C. kluyveri* and a metabolically-engineered *Escherichia coli*, which both utilize the reversed beta-oxidation pathway. The advantages of using microbiomes compared to pure cultures lies in their ability to: i. incorporate carbon from complex streams due to a broad-substrate spectrum; ii. maintain functionality even with non-sterile input; and iii. be resilient in response to disturbances.

Results and Discussion: Linking the 16S rRNA gene and shotgun metagenomic sequencing surveys. Analysis of the 16S rRNA gene sequencing effort found five abundant OTUs that were significantly correlated (r>0.8 and p<0.05) with increasing n-caproic acid production rates (FIG. 15A and Table 1). The OTUs were of various taxonomies, indicating that a range of bacteria played important roles in conversion of yeast-fermentation beer to n-caproic acid. To more specifically determine the roles of the OTUs, and to provide more certainty as to which bacteria were responsible for chain elongation, a shotgun metagenomic sequencing analysis of bioreactor samples was performed. Taxonomic analysis of the seven genes most significantly correlated with production rates of n-caproic acid (FIG. 22) suggested the importance of some of the same taxonomic groups as the 16S rRNA gene sequencing analysis (genus *Clostridium* and family Ruminococcaceae). Seven genera made up most of the reads assigned to the seven genes, and four of those (*Ethanoligenens* [family Ruminococcaceae], *Desulfitobacterium, Clostridium*, and *Propionibacterium*) increased as n-caproic acid production rates increased. To determine the probable roles of the 7 important genera, the taxonomic breakdown of genes catalyzing what are likely to be the most important carbon metabolism pathways in the bioreactor were examined Compared to the taxonomic breakdown of all reads, *Ethanoligenens* and *Bifidobacterium* were relatively abundant in starch hydrolysis and xylan metabolism, respectively, indicating that they may have been important in retrieving carbon from complex substrate molecules. *Clostridium* spp. strongly dominated the chain-elongation gene pool, reflecting their important role in the terminal process for n-caproic acid formation.

TABLE 1

Correlation coefficient (with significance) for OTUs whose relative abundance was positively correlated to the n-caproic acid production rate (with 16S rRNA gene sequencing analysis).

| OTU | Significance (p-value) | Correlation Coefficient (r) | Phyla | Class | Order | Family |
|---|---|---|---|---|---|---|
| [1]466 | 0.002 | 0.960 | p__Firmicutes | c__Clostridia | o__Clostridiales | f__Clostridiales_Family_XI_Incertae_Sedis |
| [1]733 | 0.008 | 0.926 | p__Firmicutes | c__Clostridia | o__Clostridiales | f__Ruminococcaceae |
| 746 | 0.008 | 0.926 | [2] | | | |
| 260 | 0.010 | 0.917 | p__Fimicutes | c__Clostridia | o__Clostridiales | f__Ruminococcaceae |
| 521 | 0.011 | 0.912 | p__Firmicutes | c__Clostridia | o__Clostridiales | f__Clostridiaceae |
| [1]2 | 0.015 | 0.899 | [2] | | | |
| [1]97 | 0.015 | 0.897 | [2] | | | |

TABLE 1-continued

Correlation coefficient (with significance) for OTUs whose relative abundance was positively correlated to the n-caproic acid production rate (with 16S rRNA gene sequencing analysis).

| OTU | Significance (p-value) | Correlation Coefficient (r) | Phyla | Class | Order | Family |
|---|---|---|---|---|---|---|
| [1]225 | 0.016 | 0.895 | p__Firmicutes | c__Clostridia | o__Clostridiales | f__Clostridiaceae |
| 649 | 0.027 | 0.864 | p__Firmicutes | c__Clostridia | o__Clostridiales | f__Ruminococcaceae |
| 792 | 0.033 | 0.849 | p__Firmicutes | c__Clostridia | o__Clostridiales | f__Ruminococcaceae |
| 674 | 0.041 | 0.830 | p__Firmicutes | | | |
| 551 | 0.052 | 0.808 | p__Firmicutes | c__Clostridia | o__Clostridiales | f__Ruminococcaceae |
| 123 | 0.070 | 0.776 | p__Firmicutes | c__Clostridia | o__Clostridiales | f__Ruminococcaceae |
| 509 | 0.086 | 0.749 | p__Firmicutes | c__Clostridia | o__Clostridiales | f__Clostridiaceae |
| 13 | 0.097 | 0.734 | p__Firmicutes | c__Clostridia | o__Clostridiales | f__Ruminococcaceae |
| 695 | 0.098 | 0.732 | p__Firmicutes | c__Clostridia | o__Clostridiales | f__Ruminococcaceae |
| 289 | 0.099 | 0.731 | p__Firmicutes | c__Clostridia | o__Clostridiales | f__Clostridiaceae |
| 251 | 0.099 | 0.731 | p__Firmicutes | c__Clostridia | o__Clostridiales | f__Clostridiaceae |
| 26 | 0.106 | 0.721 | p__Firmicutes | c__Clostridia | o__Clostridiales | f__Ruminococcaceae |
| 406 | 0.112 | 0.712 | p__Bacteroidetes | c__Bacteroidia | o__Bacteroidales | f__Porphyromonadaceae |
| 631 | 0.134 | 0.684 | [2] | | | |
| 463 | 0.135 | 0.683 | p__Firmicutes | c__Clostridia | o__Clostridiales | f__Ruminococcaceae |
| 38 | 0.140 | 0.677 | p__Firmicutes | c__Clostridia | o__Clostridiales | f__Ruminococcaceae |
| 578 | 0.152 | 0.662 | p__Firmicutes | c__Clostridia | o__Clostridiales | f__Ruminococcaceae |
| 415 | 0.247 | 0.561 | p__Firmicutes | c__Clostridia | o__Clostridiales | f__Ruminococcaceae |
| 287 | 0.253 | 0.555 | p__Firmicutes | c__Clostridia | o__Clostridiales | f__Ruminococcaceae |
| 680 | 0.254 | 0.554 | p__Firmicutes | c__Clostridia | o__Clostridiales | f__Ruminococcaceae |
| 259 | 0.287 | 0.523 | p__Firmicutes | c__Clostridia | o__Clostridiales | f__Ruminococcaceae |
| 441 | 0.305 | 0.507 | p__Firmicutes | c__Clostridia | o__Clostridiales | f__Ruminococcaceae |
| 284 | 0.332 | 0.483 | [2] | | | |
| 673 | 0.370 | 0.450 | p__Firmicutes | c__Clostridia | o__Clostridiales | f__Ruminococcaceae |
| 374 | 0.378 | 0.444 | p__Firmicutes | c__Clostridia | o__Clostridiales | f__Ruminococcaceae |
| 180 | 0.380 | 0.442 | p__Firmicutes | | | |
| 586 | 0.380 | 0.442 | p__Firmicutes | c__Clostridia | o__Clostridiales | f__Ruminococcaceae |
| 286 | 0.419 | 0.410 | p__Firmicutes | c__Clostridia | o__Clostridiales | f__Ruminococcaceae |
| 33 | 0.422 | 0.408 | p__Firmicutes | c__Clostridia | o__Clostridiales | f__Ruminococcaceae |
| 144 | 0.433 | 0.400 | p__Firmicutes | c__Clostridia | o__Clostridiales | f__Ruminococcaceae |
| 497 | 0.434 | 0.398 | p__Firmicutes | c__Clostridia | o__Clostridiales | f__Ruminococcaceae |
| 637 | 0.449 | 0.386 | p__Firmicutes | c__Clostridia | o__Clostridiales | f__Ruminococcaceae |
| 620 | 0.528 | 0.326 | p__Firmicutes | c__Clostridia | o__Clostridiales | f__Ruminococcaceae |
| 490 | 0.531 | 0.324 | p__Firmicutes | c__Clostridia | o__Clostridiales | f__Clostridiaceae |
| 278 | 0.576 | 0.291 | p__Firmicutes | c__Clostridia | o__Clostridiales | f__Ruminococcaceae |
| 402 | 0.582 | 0.286 | p__Firmicutes | c__Clostridia | o__Clostridiales | f__Clostridiaceae |
| 689 | 0.625 | 0.255 | p__Firmicutes | c__Clostridia | o__Clostridiales | f__Clostridiaceae |
| 719 | 0.646 | 0.241 | p__Firmicutes | c__Clostridia | o__Clostridiales | f__Ruminococcaceae |
| 282 | 0.649 | 0.239 | p__Firmicutes | c__Clostridia | o__Clostridiales | f__Ruminococcaceae |
| 176 | 0.678 | 0.218 | [2] | | | |
| 369 | 0.685 | 0.214 | p__Firmicutes | c__Clostridia | o__Clostridiales | f__Ruminococcaceae |
| 550 | 0.695 | 0.206 | p__Firmicutes | c__Clostridia | o__Clostridiales | f__Ruminococcaceae |
| 457 | 0.723 | 0.187 | p__Firmicutes | c__Clostridia | o__Clostridiales | f__Ruminococcaceae |
| 1 | 0.761 | 0.161 | p__Firmicutes | c__Clostridia | o__Clostridiales | f__Ruminococcaceae |
| 742 | 0.771 | 0.154 | p__Firmicutes | c__Clostridia | o__Clostridiales | f__Ruminococcaceae |
| 440 | 0.802 | 0.133 | p__Firmicutes | c__Clostridia | o__Clostridiales | f__Lachnospiraceae |
| 428 | 0.860 | 0.094 | p__Bacteroidetes | c__Bacteroidia | o__Bacteroidales | |
| 119 | 0.919 | 0.054 | p__Firmicutes | c__Clostridia | o__Clostridiales | f__Ruminococcaceae |
| 439 | 0.967 | 0.022 | p__Firmicutes | c__Clostridia | o__Clostridiales | f__Ruminococcaceae |
| 803 | 0.975 | 0.017 | p__Firmicutes | c__Clostridia | o__Clostridiales | f__Ruminococcaceae |

[1]OTUs with r >0.80 and p-value <0.05 and whose relative abundance reached at least 0.05 by day 90.
[2]OTUs without taxonomic information could only be identified as belonging to the domain bacteria.

TABLE 2

Genes included in the analysis (with shotgun metagenomic sequencing analysis). Only those genes with >1000 assigned reads are included in the figure.

| Pathway Involvement | EC Number | Name | >1000 Reads |
|---|---|---|---|
| Starch to Glycolysis | 2.4.1.1 | Phosphorylase | Yes |
| Xylan/Xylose to Xylulose | 3.2.1.3.7 | Xylan 1,4-β-Xylosidase | Yes |
| | 1.1.1.21 | Aldehyde Reductase | No |
| | 1.1.1.9 | D-Xylulose Reductase | Yes |
| | 5.3.1.5 | Xylose Isomerase | Yes |
| | 2.7.1.17 | Xylulokinase | No |
| [1]Xylulose to Glycolysis | 2.2.1.1 | Transketolase | Yes |
| Cellulose to Glycolysis | 3.2.1.4 | Cellulase | No |
| | 3.2.1.91 | Cellulose 1,4-β-cellobiosidase | No |
| | 3.2.1.21 | β-glucosidase | Yes |
| | 2.7.1.1 | Hexokinase | No |
| | 2.7.1.2 | Glucokinase | No |

TABLE 2-continued

Genes included in the analysis (with shotgun metagenomic sequencing analysis). Only those genes with >1000 assigned reads are included in the figure.

| Pathway Involvement | EC Number | Name | >1000 Reads |
|---|---|---|---|
| | 2.7.1.63 | Polyphosphate-glucose phosphotransferase | No |
| | 5.1.3.15 | Glucose-6-phosphate 1-epimerase | No |
| | 5.1.3.3 | Aldose 1-epimerase | No |
| Glycolysis to Pyruvate | 5.4.2.2 | Phosphoglucomutase | Yes |
| | 5.3.1.9 | Glucose 6-phosphate isomerase | Yes |
| | 2.7.1.11 | 6-Phosphofructokinase | Yes |
| | 2.7.1.146 | ADP-specific phosphofructokinase | No |
| | 4.1.2.13 | Fructose-biphosphate aldolase | Yes |
| | 1.2.1.12 | Glyceraldehyde 3-phosphate dehydrogenase | Yes |
| | 1.2.1.59 | Glyceraldehyde 3-phosphate dehydrogenase (NADP) | No |
| | 5.3.1.1 | Triose-phosphate isomerase | Yes |
| | 2.7.2.3 | Phospholycerate kinase | Yes |
| | 5.4.2.4 | Bisphosphoglycerate mutase | No |
| | 3.1.3.13 | Bisphosphoglycerate phosphatase | No |
| | 5.4.2.1 | Phosphoglycerate mutase | Yes |
| | 4.2.1.11 | Phosphopyruvate hydratase | Yes |
| | 2.7.1.40 | Pyruvate kinase | No |
| Pyruvate to Acetyl-CoA | 2.3.1.54 | Formate C-acetyltransferase (Pyruvate-formate lyase) | Yes |
| Ethanol to Acetyl-CoA | 1.1.1.1 | Alcohol dehydrogenase | Yes |
| | 1.1.1.2 | Alcohol dehydrogenase (NADP) | No |
| | 1.2.1.3 | Aldehyde dehydrogenase (NAD) | No |
| | 1.2.1.5 | Aldehyde dehydrogenase (NADP) | No |
| Chain Elongation | 2.3.1.9 | Acetyl-CoA C-acetyltransferase | Yes |
| | 1.1.1.36 | Acetoacetyl-CoA reductase | No |
| | 1.1.1.35 | 3-Hydroxylacyl-CoA dehydrogenase | No |
| | 1.1.1.157 | 3-Hyroxybutyryl-CoA dehydrogenase | Yes |
| | 4.2.1.55 | 3-Hydroxybutyryl-CoA dehydratase | Yes |
| | 4.2.1.17 | Enoyl-CoA hydratase | No |
| | 1.3.8.1 | Butyryl-CoA dehydrogenase | Yes |
| | 2.8.3.6 | 3-Oxoadipate CoA transferase | No |

[1]The transketolase involved in conversion of xylulose to a glycolysis intermediate is separated from other xylan degradation genes because the taxonomy distribution of the gene was very different.

TABLE 3

Coefficient of correlation to n-caproic acid production rate for genes included in the analysis (with shotgun metagenomic sequencing analysis). Only those genes with >1000 assigned reads are included.

| EC Number | Name | Correlation Coefficient [r | r$^2$] | >1000 Reads |
|---|---|---|---|
| 2.4.1.7 | Sucrose phosphorylase | 0.98 | 0.95 | Yes |
| 2.4.2.2 | Pyrimidine-nucleoside phosphorylase | 0.97 | 0.94 | Yes |
| 1.17.4.2 | Robonucleoside-triphosphate reductase | 0.96 | 0.94 | Yes |
| 5.4.2.7 | Phosphopentomutase | 0.96 | 0.92 | Yes |
| 4.2.3.3 | Methylglyoxal synthase | 0.96 | 0.92 | Yes |
| 5.4.2.8 | Phosphomannomutase | 0.95 | 0.91 | Yes |
| 5.4.3.3 | β-lysine 5,6 aminomutase | 0.95 | 0.91 | No |
| 2.2.1.1 | Transketolase | 0.95 | 0.90 | Yes |

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A method for obtaining a product comprising $C_6$ and/or $C_8$ carboxylates and/or methane from a carbohydrate containing biomass comprising the steps of:
    a) contacting the carbohydrate containing biomass, an alcohol, and a mixture of microorganisms in a vessel to form a reaction mixture,
    b) maintaining the reaction mixture under anaerobic conditions at 15° C. to 40° C., a pH of from 4 to 6, and a hydrogen partial pressure of from 0.2 atm to 5 atm such that $C_6$ and/or $C_8$ carboxylates and/or methane are formed in the reaction mixture, and
    c) separating at least a portion of the $C_6$ and/or $C_8$ carboxylates and/or methane from the reaction mixture to obtain the product,
wherein less than 5% of input carbon is lost as carbon dioxide.

2. The method of claim 1, wherein the alcohol is ethanol.

3. The method of claim 1, wherein the product has a gaseous component and a liquid component.

4. The method of claim 3, wherein the product comprises $C_6$ carboxylates.

5. The method of claim 3, wherein the gaseous component comprises methane and carbon dioxide.

6. The method of claim 3, wherein the method further comprises recycling the gaseous component.

7. The method of claim 3, wherein the method further comprises separating the gaseous component from the reaction mixture.

8. The method of claim 1, wherein the method is carried out continuously by feeding the vessel continuously or semi-continuously with biomass and alcohol.

9. The method of claim 1, wherein all of the $C_6$ and/or $C_8$ carboxylates are removed to obtain the product.

10. The method of claim 1, wherein the removing of $C_6$ and/or $C_8$ carboxylates is continuous.

11. The method of claim 1, wherein the mixture of microorganisms is present in an inoculum source selected from the group consisting of activated sludge, anaerobic digesters, acidogenic processes, rumen microbes, soil microorganisms, marine microorganisms, intestinal microorganism, and feces.

12. The method of claim 1, wherein the $C_6$ and $C_8$ carboxylates are separated from the reaction mixture by a membrane-based liquid-liquid extraction using a mineral oil stripping solution comprising a species of phosphine oxide.

13. The method of claim 1, wherein the ethanol is from a feedstock.

14. The method of claim 13, wherein the feedstock is corn-to-ethanol beer or grain-based alcohol mash.

15. The method of claim 1, wherein the carbohydrate containing biomass is municipal waste, animal waste, agricultural residues, by-products of alternative energy processes, wood wastes, biosolids wastes, animal hydrolysates, waste from food production, yogurt production waste, beer production waste, animal rendering waste, or a combination thereof.

* * * * *